United States Patent [19]
Wasicak et al.

[11] Patent Number: 5,733,912
[45] Date of Patent: Mar. 31, 1998

[54] 7A-HETEROCYCLE SUBSTITUTED HEXAHYDRO-1H-PYRROLIZINE COMPOUNDS USEFUL IN CONTROLLING CHEMICAL SYNAPTIC TRANSMISSION

[75] Inventors: James T. Wasicak, Waterford, Wis.; David S. Garvey, Dover, Mass.; Mark W. Holladay, Libertyville, Ill.; Nan-Horng Lin, Mundelein, Ill.; Keith B. Ryther, Round Lake Park, Ill.

[73] Assignee: Abbott Laboratories, Abbott Park, Ill.

[21] Appl. No.: 802,978

[22] Filed: Feb. 19, 1997

[51] Int. Cl.$^6$ .......................... A61K 31/41; A61K 31/44; A61K 31/50; C07D 487/08
[52] U.S. Cl. .......................... 514/253; 514/256; 514/314; 514/339; 514/378; 514/406; 544/242; 544/238; 544/334; 544/336; 548/235; 548/364.7; 546/152; 546/276.7
[58] Field of Search ............... 546/152, 276.7; 544/242, 238, 334, 336; 548/235, 364.7; 514/253, 256, 314, 339, 378, 406

[56] References Cited

U.S. PATENT DOCUMENTS

| | | | |
|---|---|---|---|
| 4,582,836 | 4/1986 | Carmosin et al. | 514/299 |
| 4,617,401 | 10/1986 | Miyano et al. | 548/453 |
| 4,689,329 | 8/1987 | Carmosin et al. | 514/299 |
| 4,800,207 | 1/1989 | Carmosin et al. | 514/413 |
| 4,971,975 | 11/1990 | Hadley et al. | 514/299 |
| 5,132,316 | 7/1992 | Hadley et al. | 514/361 |
| 5,177,084 | 1/1993 | Baker et al. | 514/305 |
| 5,217,975 | 6/1993 | Wadsworth et al. | 514/299 |
| 5,242,927 | 9/1993 | Baker et al. | 514/299 |
| 5,260,293 | 11/1993 | Baker et al. | 514/214 |
| 5,260,314 | 11/1993 | Sauerberg et al. | 514/305 |
| 5,262,427 | 11/1993 | Nielson et al. | 514/304 |
| 5,472,958 | 12/1995 | Gunn, Jr. et al. | 514/210 |
| 5,567,710 | 10/1996 | Whitten et al. | 514/292 |
| 5,629,325 | 5/1997 | Lin et al. | 514/318 |

FOREIGN PATENT DOCUMENTS

| | | |
|---|---|---|
| 0039903 | 5/1981 | European Pat. Off. |
| 0239309 | 3/1987 | European Pat. Off. |
| 0261763 | 6/1987 | European Pat. Off. |
| 0287356 | 4/1988 | European Pat. Off. |
| 0296721 | 5/1988 | European Pat. Off. |
| 0301729 | 7/1988 | European Pat. Off. |
| 0307140 | 9/1988 | European Pat. Off. |
| 0307141 | 9/1988 | European Pat. Off. |
| 0307142 | 9/1988 | European Pat. Off. |
| 0316718 | 11/1988 | European Pat. Off. |
| 0322182 | 12/1988 | European Pat. Off. |
| 0323864 | 1/1989 | European Pat. Off. |
| 0327155 | 1/1989 | European Pat. Off. |
| 0328200 | 2/1989 | European Pat. Off. |
| 0339834 | 4/1989 | European Pat. Off. |
| 0363085 | 9/1989 | European Pat. Off. |
| 0366304 | 10/1989 | European Pat. Off. |
| 0402056 | 5/1990 | European Pat. Off. |
| 0412798 | 8/1990 | European Pat. Off. |
| 0413545 | 8/1990 | European Pat. Off. |
| 0427390 | 9/1990 | European Pat. Off. |
| 0445731 | 3/1991 | European Pat. Off. |
| 0459568 | 5/1991 | European Pat. Off. |
| 0525879 | 7/1992 | European Pat. Off. |
| 9323395 | 11/1993 | European Pat. Off. |
| 9420496 | 9/1994 | European Pat. Off. |
| 9113885 | 9/1991 | WIPO |
| 9203433 | 3/1992 | WIPO |
| 9206959 | 4/1992 | WIPO |
| 9314090 | 7/1993 | WIPO |

OTHER PUBLICATIONS

Reinecke et al, The Peripheral Synthesis of Medium Ring Nitrogen Heterycles Displacement Reactions; J. Org. Chem 37 No. 22 1972.

Leonard et al., Unsaturated Amines V. The Attack of Ternary Iminium Compounds by Nucleophilic Reagents; JACS, 78, 19, 1956.

Brioni et al., In Viv Profile of Novel Nicotinic Ligands with CNS Selectivity; Med Chem Res (1996) 487–510.

Badio et al., Antinociceptive Effects of the Alkaloid Epibatidine; Further Studies on Involvement of Nicotinic Receptors; Drug Develop. Research 36:46–59(1995).

Korczyn, Parkinson's Disease Psychopharmacology: The Fourth Generation of Progress, Raven Press, New York, 1995.

Roth et al., Biochemical Pharmacology of Midbrain Dopamine Neurons; Psychopharmacology: The Fourth Generation of Progress, Raven Press, New York, 1995.

*Primary Examiner*—Fiona T. Powers
*Attorney, Agent, or Firm*—Frank Z. Yang

[57] ABSTRACT

7a-Substituted hexahydro-1H-pyrrolizine compounds having the formula

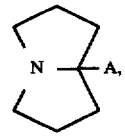

wherein A is a defined heterocycle moiety, pharmaceutical compositions of these compounds, and use of said compositions to selectively control synaptic transmission in mammals.

7 Claims, No Drawings

7A-HETEROCYCLE SUBSTITUTED HEXAHYDRO-1H-PYRROLIZINE COMPOUNDS USEFUL IN CONTROLLING CHEMICAL SYNAPTIC TRANSMISSION

TECHNICAL FIELD

This invention relates to 7a-heterocycle-substituted hexahydro-1H-pyrrolizine compounds which control chemical synaptic transmission; to therapeutically effective pharmaceutical compositions of these compounds;and to the use of said compositions to control synaptic transmission in mammals.

BACKGROUND OF THE INVENTION

Compounds that selectively control chemical synaptic transmission offer therapeutic utility in treating disorders that are associated with dysfunctions in synaptic transmission. This utility may arise from controlling either presynaptic or post-synaptic chemical transmission. The control of synaptic chemical transmission is, in turn, a direct result of a modulation of the excitability of the synaptic membrane. Presynaptic control of membrane excitability results from the direct effect an active compound has upon the organelles and enzymes present in the nerve terminal for synthesizing, storing, and releasing the neurotransmitter, as well as the process for active re-uptake. Postsynaptic control of membrane excitability results from the influence an active compound has upon the cytoplasmic organelles that respond to neurotransmitter action.

An explanation of the processes involved in chemical synaptic transmission will help to illustrate more fully the potential applications of the invention. (For a fuller explanation of chemical synaptic transmission refer to Hoffman et at., "Neurotransmission: The autonomic and somatic motor nervous systems." In: *Goodman and Gilman's. The Pharmacological Basis of Therapeutics*, 9th ed., J. G. Hardman, L. E. Limbird, P. B. Molinoff, R. W. Ruddon, and A. Goodman Gilman, eds., Pergamon Press, New York, 1996, pp. 105–139).

Typically; chemical synaptic transmission begins with a stimulus that depolarizes the transmembrane potential of the synaptic junction above the threshold that elicits an all-or-none action potential in a nerve axon. The action potential propagates to the nerve terminal where ion fluxes activate a mobilization process leading to neurotransmitter secretion and "transmission" to the postsynaptic cell. Those cells which receive communication from the central and peripheral nervous systems in the form of neurotransmitters are referred to as "excitable cells." Excitable cells are cells such as nerves, smooth muscle cells, cardiac cells and glands. The effect of a neurotransmitter upon an excitable cell may be to cause either an excitatory or an inhibitory postsynaptic potential (EPSP or IPSP, respectively) depending upon the nature of the postsynaptic receptor for particular neurotransmitter and the extent to which other neurotransmitters are present. Whether a particular neurotransmitter causes excitation or inhibition depends principally on the ionic channels that are opened in the postsynaptic membrane (i.e., in the excitable cell).

EPSPs typically result from a local depolarization of the membrane due to a generalized increased permeability to cations (notably $Na^+$ and K+), whereas IPSPs are the result of stabilization or hyperpolarization of the membrane excitability due to a increase in permeability to primarily smaller ions (including $K^+$ and $Cl^-$). For example, the neurotransmitter acetylcholine excites at skeletal muscle junctions by opening permeability channels for $Na^+$ and $K^+$. At other synapses, such as cardiac cells, acetylcholine can be inhibitory, primarily resulting from an increase in $K^+$ conductance.

The biological effects of the compounds of the present invention result from modulation of a particular subtype of acetylcholine receptor. It is, therefore, important to understand the differences between two receptor subtypes. The two distinct subfamilies of acetylcholine receptors are defined as nicotinic acetylcholine receptors and muscarinic acetylcholine receptors. (See *Goodman and Gilman's, The Pharmacological Basis of Therapeutics*, op. cit.).

The responses of these receptor subtypes are mediated by two entirely different classes of second messenger systems. When the nicotinic acetylcholine receptor is activated, the response is an increased flux of specific extracellular ions (e.g. $Na^+$, $K^+$ and $Ca^{++}$) through the neuronal membrane. In contrast, muscarinic acetylcholine receptor activation leads to changes in intracellular systems that contain complex molecules such as G-proteins and inositol phosphates. Thus, the biological consequences of nicotinic acetylcholine receptor activation are distinct from those of muscarinic receptor activation. In an analogous manner, inhibition of nicotinic acetylcholine receptors results in still other biological effects, which are distinct and different from those arising from muscarinic receptor inhibition.

As indicated above, the two principal sites to which drug compounds that affect chemical synaptic transmission may be directed are the presynaptic nerve terminal and the postsynaptic membrane. Actions of drugs directed to the presynaptic site may be mediated through presynaptic receptors that respond to the neurotransmitter which the same secreting structure has released (i.e., through an autoreceptor), or through a presynaptic receptor that responds to another neurotransmitter (i.e., through a heteroreceptor). Actions of drugs directed to the postsynaptic membrane mimic the action of the endogenous neurotransmitter or inhibit the interaction of the endogenous neurotransmitter with a postsynaptic receptor.

Classic examples of drugs that modulate postsynaptic membrane excitability are the neuromuscular blocking agents which interact with nicotinic acetylcholine-gated channel receptors on skeletal muscle, for example, competitive (stabilizing) agents, such as curare, or depolarizing agents, such as succinylcholine.

In the central nervous system, postsynaptic cells can have many neurotransmitters impinging upon them. This makes it difficult to know the precise net balance of chemical synaptic transmission required to control a given cell. Nonetheless, by designing compounds that selectively affect only one pre- or postsynaptic receptor, it is possible to modulate the net balance of all the other inputs. Obviously, the more that is understood about chemical synaptic transmission in CNS disorders, the easier it would be to design drugs to treat such disorders.

Knowing how specific neurotransmitters act in the CNS allows one to speculate about the disorders that may be treatable with certain CNS-active drugs. For example, dopamine is widely recognized as an important neurotransmitter in the central nervous systems in humans and animals. Many aspects of the pharmacology of dopamine have been reviewed by Roth and Elsworth, "Biochemical Pharmacology of Midbrain Dopamine Neurons", In: *Psychopharmacology: The Fourth Generation of Progress*, F. E. Bloom and D. J. Kupfer, Eds., Raven Press, NY, 1995, pp 227–243). Patients with Parkinson's disease have a primary loss of dopamine containing neurons of the nigrostriatal pathway, which results in profound loss of motor control. Therapeutic strategies to replace the dopamine deficiency with dopamine mimetics, as well as administering pharmacologic agents that modify dopamine release and other neurotransmitters have been found to have therapeutic benefit ("Parkinson's Disease", In: *Psychopharmacology: The Fourth Generation of Progress*, op. cit., pp 1479-1484).

Other studies have shown that certain compounds which potently affect neurotransmission at nicotinic acetylcholine receptors are effective for the relief of pain (Badio et at., *Drug Devel. Res.*, 1995, 36: 46–59)

Neuroprotective actions also have been found for several nicotinic acetylcholine receptor ligands, as reviewed in Brioni et al. *Med. Chem. Res.*, 1996, 487–510.

New and selective neurotransmitter controlling agents are still being sought, in the hope that one or more will be useful in important, but as yet poorly controlled, disease states or behavior models. For example, dementia, such as is seen with Alzheimer's disease or Parkinsonism, remains largely untreatable. Symptoms of chronic alcoholism and nicotine withdrawal involve aspects of the central nervous system, as does the behavioral disorder Attention-Deficit Disorder (ADD). Specific agents for treatment of these and related disorders are few in number or non-existent.

A more complete discussion of the possible utility as CNS-active agents of compounds with activity as cholinergic ligands selective for neuronal nicotinic receptors, (i.e., for controlling chemical synaptic transmission) may be found in U.S. Pat. No. 5,472,958, to Gun net al., issued Dec. 5, 1995, which is incorporated herein by reference.

Existing acetylcholine agonists are therapeutically suboptimal in treating the conditions discussed above. For example, such compounds have unfavorable pharmacokinetics (e.g., arecoline and nicotine), poor potency and lack of selectivity (e.g., nicotine), poor CNS penetration (e.g., carbachol) or poor oral bioavailability (e.g., nicotine). In addition, other agents have many unwanted central agonist actions, including hypothermia, hypolocomotion and tremor and peripheral side effects, including miosis, lachrymation, defecation and tachycardia (Benowitz et al., in: *Nicotine Psychopharmacology*, S. Wonnacott, M. A. H. Russell, & I. P. Stolerman, eds., Oxford University Press, Oxford, 1990, pp. 112–157; and M. Davidson, et al., in *Current Research in Alzheimer Therapy*, E. Giacobini and R. Becker, ed.; Taylor & Francis: New York, 1988; pp 333–336).

Orlek et al (PCT application WO 91/13885, published Sep. 19, 1991) disclose bridged azabicyclic compounds bearing triazine substituents having utility in enhancing acetylcholine function via action at muscarinic receptors in the central nervous system.

Hedley et al (European Patent application 287,356, published Oct. 19, 1988) disclose bridged azabicyclic compounds bearing 5-membered heteroaromatic ring substituents having utility in enhancing acetylcholine function via action at muscarinic receptors in the central nervous system.

Baker et al. (European Patent application 412,798, published Feb. 13, 1991) disclose pyridine compounds substituted with various azabicyclic ring moieties having utility in stimulating central muscarinic acetylcholine receptors.

Baker et al. (U.S. Pat. No. 5,260,293, issued Nov. 9, 1993) disclose pyrazine, pyridazine and pyrimidine compounds substituted with various azabicyclic ring moieties having utility in stimulating central muscarinic acetylcholine receptors.

Carmosin et al. (U.S. Pat. No. 4,800,207, issued Jan. 24, 1989 disclose hexahydropyrrolizines substituted with various hetero-containing ring moieties having utility in pharmaceutical compositions for treating pain.

Carmosin et al. (U.S. Pat. No. 4,582,836, issued Apr. 15, 1986 disclose octahydroindolizidines substituted with various hetero-containing ring moieties having utility in pharmaceutical compositions for treating pain.

Miyana et al. (European Patent application 39,903, published Nov. 18, 1981) disclose pyrrolizidines substituted at the 8-position with acyclic substituents having spasmolytic activity on the smooth muscle of guinea pig ileum.

SUMMARY OF THE INVENTION

It has been found, in accordance with the present invention, that certain 7a-heterocycle-substituted hexahydro-1H-pyrrolizine compounds are selective and potent cholinergic compounds useful in selectively controlling synaptic transmission.

In its principal aspect, the present invention provides a compound of formula (I) below, or a pharmaceutically acceptable salt thereof, wherein a 7a-hexahydro-1H-pyrrolizine is directly linked to a substituted 5-isoxazole, 5-pyrazole, 3-pyridine, 5-pyrimidine, 2-pyrazine, 3-pyridazine, or 3-quinoline group.

Another aspect of the present invention provides pharmaceutical compositions comprising a therapeutically effective amount of a compound of formula (I) in combination with a pharmaceutically acceptable carrier or diluent.

In yet another aspect, the present invention provides a method for selectively controlling synaptic transmission in a mammal.

A further aspect of the invention is a process for preparing compounds of formula (I).

The novel compounds of the present invention are represented by formula (I):

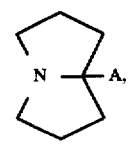
(I), or a pharmaceutically acceptable salt or pro-drug thereof wherein the group designated A is selected from the group consisting of:

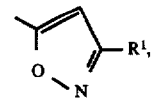
(a)

wherein $R^1$ is $C_1$–$C_3$-alkyl, as defined below, —$CH_2$-aryl, —$CH_2$-substituted-aryl, or —$CH_2$—$CH_2$-substituted-aryl, wherein aryl and substituted-aryl are as defined below;

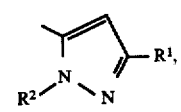
(b)

wherein $R^1$ is as defined above, and $R^2$ is H or $C_1$–$C_3$-alkyl;

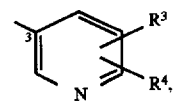
(c)

wherein
$R^3$ is substituted at the 2, 4, or 6-position and is selected from the group consisting of H, $C_1$–$C_3$-alkyl, Br, Cl, or F; and R⁴ is substituted at one of the remaining positions not occupied by R³ and is independently selected from the group consisting of H, $C_1$-$C_3$-alkyl, Br, Cl, F or $C_1$-$C_3$-alkyl-O—; or when substituted at the 5-position R⁴ may additionally be selected from the group consisting of (1) O—R⁶, wherein R⁶ is selected from the group consisting of;
  (a) hydrogen,
  (b) alkyl of one to six carbon atoms,
  (c) alkenyl of one to six carbon atoms
  (d) alkynyl of one to six carbon atoms
  (e) haloalkyl of one to six carbon atoms,
  (f) hydroxyalkyl of two to six carbon atoms,
  (h) amino,
  (i) alkylamino of one to six carbon atoms,
  (j) dialkylamino in which the two alkyl groups are independently of one to six carbon atoms,
  (k) phenyl,
  (l) naphthyl,
  (m) biphenyl,
  (n) furyl,
  (o) thienyl,
  (p) pyridinyl,
  (q) pyrazinyl,
  (r) pyridazinyl,
  (s) pyrimidinyl,
  (t) pyrrolyl,
  (u) pyrazolyl,
  (v) imidazolyl,
  (w) indolyl,
  (x) thiazolyl,
  (y) oxazolyl,
  (z) isoxazolyl,
  (aa) thiadiazolyl,
  (bb) oxadiazolyl,
  (cc) quinolinyl,
  (dd) isoquinolinyl,
  (ee) aryl-$C_1$-$C_6$-alkyl,
  (ff) heteroaryl-$C_1$-$C_6$-alkyl and
  (gg) any of the groups (i) through (ff) of R⁶ above substituted on the aromatic ring with one or two substituents independently selected from the group consisting of alkyl of one to six carbon atoms, haloalkyl of one to six carbon atoms, alkoxy of one to six carbon atoms, alkoxyalkyl in which the alkoxy and alkyl portions are independently of one to six carbon atoms, alkoxyalkoxyl in which the alkoxy portions are independently of one to six carbon atoms, halogen, cyano, hydroxy, amino, alkylamino of one to six carbon atoms, carboxyl, and alkoxycarbonyl of two to six carbon atoms;
(2) —S—R⁶, wherein R⁶ is as defined above;
(3) —N(R⁶)(R⁷), wherein R⁶ is as defined above and R⁷ is selected from H or alkyl of 1 to 6 carbon atoms;
(4) LR⁸, wherein L is absent or is selected from the group consisting of
  (a) —(CH₂)$_p$—, wherein p is 1 to 6;
  (b) —(CH=CH)$_q$—, wherein q is one or two;
  (c) —C(O)—:
  (d) —OC(O)—;
  (e) —N(R⁷)—C(O)—, wherein R⁷ is as defined above;
  (f) —CH₂—CH₂—C(O)—;
  (g) —CH₂—O—C(O)—; —CH₂—NH—C(O)—; or
  (h) —C≡C—; and wherein R⁸ is selected from the group consisting of:
  (a) hydrogen,
  (b) alkyl of one to six carbon atoms,
  (c) alkenyl of one to six carbon atoms
  (d) alkynyl of one to six carbon atoms
  (e) haloalkyl of one to six carbon atoms,
  (f) hydroxyalkyl of one to six carbon atoms,
  (g) alkoxy of one to six carbon atoms,
  (h) amino,
  (i) alkylamino of one to six carbon atoms,
  (j) dialkylamino in which the two alkyl groups are independently of one to six carbon atoms,
  (k) phenyl,
  (l) naphthyl,
  (m) biphenyl,
  (n) furyl,
  (o) thienyl,
  (p) pyridinyl,
  (q) pyrazinyl,
  (r) pyridazinyl,
  (s) pyrimidinyl,
  (t) pyrrolyl,
  (u) pyrazolyl,
  (v) imidazolyl,
  (w) indolyl,
  (x) thiazolyl,
  (y) oxazolyl,
  (z) isoxazolyl,
  (aa) thiadiazolyl,
  (bb) oxadiazolyl,
  (cc) quinolinyl,
  (dd) isoquinolinyl, and
  (ee) any of the groups (i) through (dd) of R⁶ above substituted with one or two substituents independently selected from the group consisting of alkyl of one to six carbon atoms, haloalkyl of one to six carbon atoms, alkoxy of one to six carbon atoms, alkoxyalkyl in which the alkoxy and alkyl portions are independently of one to six carbon atoms, alkoxyalkoxyl in which the alkoxy portions are independently of one to six carbon atoms, halogen, cyano, hydroxy, amino, alkylamino of one to six carbon atoms, carboxyl, and alkoxycarbonyl of two to six carbon atoms;

with the requirement that in groups of the type —O—R⁶, —S—R⁶, —N(R⁶)(R⁷) and L—R⁸, none of R⁶, —N(R⁶)(R⁷) or L—R⁸ may contain a nitrogen atom which is in conjugation with a double or triple bond;

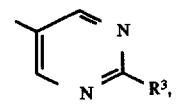

(d)

wherein R³ is as defined above;

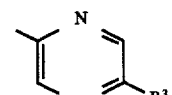

(e)

wherein R³ is as defined above;

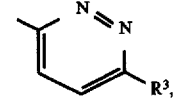

(f)

wherein R³ is as defined above; and

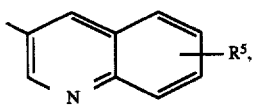

(g)

wherein R⁵ is H, C₁–C₃-alkyl, Cl or F.

DETAILED DESCRIPTION OF THE INVENTION

Certain compounds of this invention may possess one or more asymmetric centers and may exist in optically active forms. Additional asymmetric centers may be present in a substituent group, such as an alkyl group. Compounds of the invention which have one or more asymmetric carbon atoms may exist as the optically pure enantiomers, pure diastereomers, mixtures of enantiomers, mixtures of diastereomers, racemic mixtures of enantiomers, diastereomeric racemates or mixtures of diastereomeric racemates. It is to be understood that the present invention anticipates and includes within its scope all such isomers and mixtures thereof. The terms "R" and "S" used herein are configurations as defined in *IUPAC 1974 Recommendations for Section E, Fundamental Stereochemistry, Pure Appl. Chem.*, 1976, 45: 13–30. In particular, the stereochemistry at the 7a-position and the point of attachment of A, as shown in Formula (I), may independently be either (R) or (S), unless specifically noted otherwise. Chiral forms of certain compounds of this invention are contemplated and are specifically included within the scope of this invention.

"Alkoxy" refers to an alkyl group, as previously defined, attached to the parent molecular moiety through an oxygen atom. Examples of alkoxy of one to six carbon atoms include but are not limited to methoxy, ethoxy, propoxy, iso-propoxy; n-butoxy, tert-butoxy, neo-pentoxy and n-hexoxy.

The term "alkoxyalkoxy" refers to an alkoxy group, as defined above, substituted by replacement of a hydrogen atom of the alkyl portion thereof with an alkoxy group. Examples of alkoxyalkyl include but are not limited to methoxymethoxy, methoxyethoxy, ethoxyethoxy, methoxypropoxy, and the like.

The term "alkoxyalkyl" refers to an alkyl group, as defined above, substituted one or more alkoxy groups. Examples of alkoxyalkyl include methoxymethyl, methoxyethyl, hydroxypropyl, methoxypropyl, and the like.

The term "alkoxycarbonyl" refers to an alkoxy group, as defined above, connected to the parent molecular moiety by means of a carbonyl linking group. Examples of alkoxycarbonyl include methoxycarbonyl, ethoxycarbonyl, t-butoxycarbonyl, and the like.

"Alkyl" refers to a univalent alkyl radical derived by removal of a single hydrogen atom from a saturated, straight- or branched-chain hydrocarbon, and specifically "C₁–C₃-alkyl" refers to an alkyl group comprising one-to-three carbon atoms, including, methyl, ethyl, n-propyl and isopropyl. "C₁–C₆-alkyl" or "alkyl of one to six carbons atoms" refer to an alkyl group comprising one-to-six carbon atoms. "C₁–C₃-alkyl" includes methyl, ethyl, n-propyl and isopropyl; "C₁–C₆-alkyl" or "alkyl of one to six carbons atoms" includes all of the previous examples as well as butyl, isobutyl, t-butyl, pentyl, neopentyl, hexyl, and the like.

"Alkenyl" refers to a univalent alkyl radical derived by removal of a single hydrogen atom from a straight- or branched-chain hydrocarbon containing one or more double bonds. Examples of alkenyl groups include ethenyl, propenyl, butenyl, isobutenyl, pentenyl, hexenyl, heptenyl, hexadienyl, and the like.

"Alkylamino" refers to an alkyl group, as previously defined, attached to the parent molecular moiety through an NH linking group. Examples of C₁–C₃-alkylamino, comprising an alkyl of one-to-three carbon atoms attached to the NH group, include methylamino, ethylamino, n-propylamino, and isopropylamino.

"Alkynyl" refers to a univalent alkyl radical derived by removal of a single hydrogen atom from a straight- or branched-chain hydrocarbon containing one or more triple bonds. Examples of alkynyl groups include ethynyl, propynyl, butynyl, pentynyl, hexynyl, heptynyl, and the like.

The term "aryl" as used herein refers to unsubstituted carbocyclic aromatic groups including, but not limited to, phenyl, 1- or 2-naphthyl, biphenyl, and the like.

The term "aryl-C₁–C₆-alkyl" refers to a C₁–C₆-alkyl group as defined above substituted by replacing one of the hydrogen atoms on the alkyl group with a aryl group, as defined herein.

Dialkylamino refers to two alkyl groups, as previously defined, attached to the parent molecular moiety through an N atom linking group. Examples of dialkylamino groups of one-to-three carbon atoms include dimethylamino, diethylamino, di-n-propylamino, and di-isopropylamino.

"Haloalkyl" refers to an alkyl group, as defined above, of one-to-six carbon atoms substituted by one or more halogen atoms and includes, for example, trifluoromethyl, chloroethyl, bromobutyl, and the like.

The term "heteroaryl", as used herein, refers to a cyclic aromatic radical having from five to ten ring atoms of which one ring atom is selected from S, O and N; zero, one or two ring atoms are additional heteroatoms independently selected from S, O and N; and the remaining ring atoms are carbon, the radical being joined to the rest of the molecule via any of the ring atoms, including but not limited to, furyl, thienyl, pyridinyl, pyrazinyl, pyridazinyl, pyrimidinyl, pyrrolyl, pyrazolyl, imidazolyl, indolyl, thiazolyl, oxazolyl, isoxazolyl, thiadiazolyl, oxadiazolyl, quinolinyl, isoquinolinyl, and the like.

The term "heteroaryl-C₁–C₆-alkyl" refers to a C₁–C₆-alkyl group as defined above substituted by replacing one of the hydrogen atoms on the alkyl group with a heteroaryl group, as defined above.

The term "hydroxyalkyl" refers to an alkyl group, as defined above, substituted with one or more hydroxy groups. Examples of hydroxyalkyl include hydroxymethyl, hydroxyethyl, hydroxypropyl, hydroxypentyl, and the like.

"Substituted alkenyl" refers to an alkenyl group, as defined above, substituted with one or more groups selected from halogen, hydroxy, alkoxy, amino, alkylamino, or dialkylamino, CN, and the like. Examples of substituted alkenyl groups include methoxyethenyl, chloropropenyl, dimethylaminobutenyl, and the like.

"Substituted alkynyl" refers to an alkynyl group, as defined, above, substituted with one or more groups selected from halogen, hydroxy, alkoxy, amino, alkylamino, or dialkylamino, CN, and the Like. Examples of substituted alkynyl groups include methoxyethynyl, chloropropynyl, dimethylaminobutynyl, and the like.

The term "substituted aryl" as used herein refers to an aryl group as defined above substituted with one or two substituents independently selected from the group consisting of alkyl of one to six carbon atoms, haloalkyl of one to six carbon atoms, alkoxy of one to six carbon atoms, alkoxyalkyl in which the alkoxy and alkyl portions are independently of one to six carbon atoms, alkoxyalkoxyl in which the alkoxy portions are independently of one to six carbon atoms, halogen, cyano, hydroxy, amino, alkylamino of one to six carbon atoms, carboxyl, and alkoxycarbonyl of two to six carbon atoms. A preferred substitution is by replacement of 1 or 2 hydrogen atoms with F, Cl, Br, $C_1$–$C_3$-alkyl, as defined above, or $C_1$–$C_3$-alkoxy. Example of substituted aryl radicals include, but are not limited to, 4-methylphenyl, 4-chlorophenyl, 4-methoxyphenyl, 4-bromophenyl, 4-fluorophenyl, 2,4-difluorophenyl, 4-methyl-1-naphthyl and 8-chloro-2-naphthyl.

The term "substituted heteroaryl" as used herein refers to a heteroaryl group as defined above substituted with one or two substituents independently selected from the group consisting of alkyl of one to six carbon atoms, haloalkyl of one to six carbon atoms, alkoxy of one to six carbon atoms, alkoxyalkyl in which the alkoxy and alkyl portions are independently of one to six carbon atoms, alkoxyalkoxyl in which the alkoxy portions are independently of one to six carbon atoms, halogen, cyano, hydroxy, amino, alkylamino of one to six carbon atoms, carboxyl, and alkoxycarbonyl of two to six carbon atoms.

One or more asymmetric centers may exist in the compounds of the present invention. Except where otherwise noted, the present invention contemplates the various stereoisomers and mixtures thereof.

As used herein, the term "pharmaceutically acceptable salt" refers to those salts which are, within the scope of sound medical judgment, suitable for use in contact with the tissues of humans and lower animals without undue toxicity, irritation, allergic response and the like, and are commensurate with a reasonable benefit/risk ratio. Pharmaceutically acceptable salts are well known in the art. For example, S. M. Berge, et al. describe pharmaceutically acceptable salts in detail in *J. Pharmaceutical Sciences*, 66: 1–19 (1977), incorporated herein by reference. The salts can be prepared in situ during the final isolation and purification of the compounds of the invention, or separately by reacting the free base function with a suitable organic acid. Examples of pharmaceutically acceptable, nontoxic acid addition salts are salts of an amino group formed with inorganic acids such as hydrochloric acid, hydrobromic acid, phosphoric acid, sulfuric acid and perchloric acid or with organic acids such as acetic acid, oxalic acid, maleic acid, tartaric acid, citric acid, succinic acid or malonic acid or by using other methods used in the art such as ion exchange. Other pharmaceutically acceptable salts include adipate, alginate, ascorbate, aspartate, benzenesulfonate, benzoate, bisulfate, borate, butyrate, camphorate, camphorsulfonate, citrate, cyclopentanepropionate, digluconate, dodecylsulfate, ethanesulfonate, formate, fumarate, glucoheptonate, glycerophosphate, gluconate, hemisulfate, heptanoate, hexanoate, hydroiodide, 2-hydroxy-ethanesulfonate, lactobionate, lactate, laurate, lauryl sulfate, malate, maleate, malonate, methanesulfonate, 2-naphthalenesulfonate, nicotinate, nitrate, oleate, oxalate, palmitate, pamoate, pectinate, persulfate, 3-phenylpropionate, phosphate, pictate, pivalate, propionate, stearate, succinate, sulfate, tartrate, thiocyanate, p-toluenesulfonate, undecanoate, valerate salts, and the like. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate.

The term "prodrug" refers to compounds that are rapidly transformed in vivo to yield the parent compounds of Formula (I), as for example, by hydrolysis in blood. T. Higuchi and V. Stella provide a thorough discussion of the prodrug concept in *Prodrugs as Novel Delivery Systems*, Vol. 14 of the A.C.S. Symposium Series, American Chemical Society (1975). Examples of esters useful as prodrugs for compounds containing carboxyl groups may be found on pages 14–21 of *Bioreversible Carriers in Drug Design: Theory and Application*, edited by E. B. Roche, Pergamon Press (1987).

The term "prodrug ester group" refers to any of several ester-forming groups that are hydrolyzed under physiological conditions. Examples of prodrug ester groups include pivoyloxymethyl, acetoxymethyl, phthalidyl, indanyl and methoxymethyl, as well as other such groups known in the art.

As used herein, the term "pharmaceutically acceptable ester" refers to esters which hydrolyze in vivo and include those that break down readily in the human body to leave the parent compound or a salt thereof. Suitable ester groups include, for example, those derived from pharmaceutically acceptable aliphatic carboxylic acids, particularly alkanoic, alkenoic, cycloalkanoic and alkanedioic acids, in which each alkyl or alkenyl moiety advantageously has not more than 6 carbon atoms. Examples of particular esters includes formates, acetates, propionates, burryates, acrylates and ethylsuccinates.

The pharmaceutical compositions of the present invention comprise a therapeutically effective amount of a compound of the present invention formulated together with one or more pharmaceutically acceptable carriers. As used herein, the term "pharmaceutically acceptable carder" means a non-toxic, inert solid, semi-solid or liquid filer, diluent, encapsulating material or formulation auxiliary of any type. Some examples of materials which can serve as pharmaceutically acceptable carriers are sugars such as lactose, glucose and sucrose; starches such as corn starch and potato starch; cellulose and its derivatives such as sodium carboxymethyl cellulose, ethyl cellulose and cellulose acetate; powdered tragacanth; malt; gelatin; talc; excipients such as cocoa butter and suppository waxes; oils such as peanut oil, cottonseed oil; safflower oil; sesame oil; olive oil; corn oil and soybean oil; glycols; such a propylene glycol; esters such as ethyl oleate and ethyl laurate; agar; buffering agents such as magnesium hydroxide and aluminum hydroxide; alginic acid; pyrogen-free water; isotonic saline; Ringer's solution; ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives and antioxidants can also be present in the composition, according to the judgment of the formulator. The pharmaceutical compositions of this invention can be administered to humans and other animals orally, rectally, parenterally, intracisternally, intravaginally, intraperitoneally, topically (as by powders, ointments, or drops), bucally, or as an oral or nasal spray.

Liquid dosage forms for oral administration include pharmaceutically acceptable emulsions, microemulsions, solutions, suspensions, syrups and elixirs. In addition to the active compounds, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, propylene glycol, 1,3-butylene glycol, dimethylformamide, oils (in particular, cottonseed, groundnut, corn, germ, olive, castor, and sesame oils), glycerol, tetrahydrofurfuryl alcohol, polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents.

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

The injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of a drug, it is often desirable to slow the absorption of the drug from subcutaneous or intramuscular injection. This may be accomplished by the use of a liquid suspension of crystalline or amorphous material with poor water solubility. The rate of absorption of the drug then depends upon its rate of dissolution which, in turn, may depend upon crystal size and crystalline form. Alternatively, delayed absorption of a parenterally administered drug form is accomplished by dissolving or suspending the drug in an oil vehicle. Injectable depot forms are made by forming microencapsulated matrices of the drug in biodegradable polymers such as polylactide-polyglycolide. Depending upon the ratio of drug to polymer and the nature of the particular polymer employed, the rate of drug release can be controlled. Examples of other biodegradable polymers include poly(orthoesters) and poly(anhydrides) Depot injectable formulations are also prepared by entrapping the drug in liposomes or microemulsions which are compatible with body tissues.

Compositions for rectal or vaginal administration are preferably suppositories which can be prepared by mixing the compounds of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, the active compound is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled gelatin capsules using such excipients as lactose or milk sugar as well as high molecular weight polyethylene glycols and the like.

The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Solid compositions of a similar type may also be employed as fillers in soft and hard-filled gelatin capsules using such excipients as lactose or milk sugar as well as high molecular weight polyethylene glycols and the like.

The active compounds can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions which can be used include polymeric substances and waxes.

Dosage forms for topical or transdermal administration of a compound of this invention include ointments, pastes, creams, lotions, gels, powders, solutions, sprays, inhalants or patches. The active component is admixed under sterile conditions with a pharmaceutically acceptable carder and any needed preservatives or buffers as may be required. Ophthalmic formulation, ear drops, eye ointments, powders and solutions are also contemplated as being within the scope of this invention.

The ointments, pastes, creams and gels may contain, in addition to an active compound of this invention, excipients such as animal and vegetable fats, oils, waxes, paraffins, starch, tragacanth, cellulose derivatives, polyethylene glycols, silicones, bentonites, silicic acid, talc and zinc oxide, or mixtures thereof.

Powders and sprays can contain, in addition to the compounds of this invention, excipients such as lactose, talc, silicic acid, aluminum hydroxide, calcium silicates and polyamide powder, or mixtures of these substances. Sprays can additionally contain customary propellants such as chlorofluorohydrocarbons.

Transdermal patches have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to the methods of treatment of the present invention, disorders in synaptic transmission are treated or prevented in a patient such as a human or lower mammal by administering to the patient a therapeutically effective amount of a compound of the invention, in such amounts and for such time as is necessary to achieve the desired result. By a "therapeutically effective amount" of a compound of the invention is meant a sufficient amount of the compound to treat disorders in synaptic transmission, at a reasonable benefit/risk ratio applicable to any medical treatment. It will be understood, however, that the total daily usage of the compounds and compositions of the present invention will be decided by the attending physician within the scope of sound medical judgment. The specific therapeutically effective dose level for any particular patient will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed; and like factors well known in the medical arts.

The total daily dose of the compounds of this invention administered to a human or other mammal in single or in divided doses can be in amounts, for example, from 0.001 to 50 mg/kg body weight or more usually from 0.01 to 25 mg/kg body weight. Single dose compositions may contain such amounts or submultiples thereof to make up the daily dose. In general, treatment regimens according to the present invention comprise administration to a patient in need of such treatment from about 1 mg to about 1000 mg of the compound(s) of this invention per day in single or multiple doses.

In a preferred embodiment of the present invention, there are provided compounds of Formula (I) above wherein A is selected from the options (a) and (c).

In a more preferred embodiment of the present invention, there are provided compounds of Formula (I) above wherein A is selected from option (c).

Representative of the compounds of the invention are:

7a-(3-methyl-5-isoxazolyl)-hexahydro-1H-pyrrolizine;
7a-(1H-3-methyl-5-pyrazolyl)-hexahydro-1H-pyrrolizine;
7a-(3-pyridinyl)-hexahydro-1H-pyrrolizine;
7a-(3-quinolinyl)-hexahydro-1H-pyrrolizine;
7a-(6-chloro-3-pyridinyl)-hexahydro-1H-pyrrolizine;
7a-(2-fluoro-3-pyridinyl)-hexahydro-1H-pyrrolizine;
7a-(2-chloro-3-pyridinyl)-hexahydro-1H-pyrrolizine;
7a-(5,6-dichloro-3-pyridinyl)-hexahydro-1H-pyrrolizine;
7a-(5-pyrimidinyl)-hexahydro-1H-pyrrolizine;
7a-(2,6-difluoro-3-pyridinyl)-hexahydro-1H-pyrrolizine;
7a-(2,6-dichloro-3-pyridinyl)-hexahydro-1H-pyrrolizine;
7a-(6-fluoro-3-pyridinyl)-hexahydro-1H-pyrrolizine;
7a-(3-ethyl-5-isoxazolyl)-hexahydro-1H-pyrrolizine;
7a-(3-propyl-5-isoxazolyl)-hexahydro-1H-pyrrolizine;
7-(3-benzyl-5-isoxazolyl)-hexahydro-1H-pyrrolizine;
7-(5-hydroxy-3-pyridinyl)-hexahydro-1H-pyrrolizine;
7-(5-benzyloxy-3-pyridinyl)-hexahydro-1H-pyrrolizine;
7-(5-bromo-3-pyridinyl)-hexahydro-1H-pyrrolizine;
7-(6-fluoro-5-methyl-3-pyridinyl)-hexahydro-1H-pyrrolizine;
7-(6-chloro-5-methyl-3-pyridinyl)-hexahydro-1H-pyrrolizine;
7-(6-methyl-3-pyridinyl)-hexahydro-1H-pyrrolizine;
7-(5-methyl-3-pyridinyl)-hexahydro-1H-pyrrolizine;
7-(5-bromo-6-fluoro-3-pyridinyl)-hexahydro-1H-pyrrolizine;
7-(5-chloro-6-fluoro-3-pyridinyl)-hexahydro-1H-pyrrolizine;
7-(4-methyl-3-pyridinyl)-hexahydro-1H-pyrrolizine;
7-(5-phenyl-3-pyridinyl)-hexahydro-1H-pyrrolizine; and
or a pharmaceutically acceptable salt or prodrug thereof.

Further included within the scope of the present invention are pharmaceutical compositions comprising one or more of the compounds of formula (I) prepared and formulated in combination with one or more non-toxic pharmaceutically acceptable compositions, in the manner described below.

Compositions suitable for parenteral injection may comprise pharmaceutically acceptable sterile aqueous or non-aqueous solutions, dispersions, suspensions or emulsions and sterile powders for reconstitution into sterile injectable solutions or dispersions. Examples of suitable aqueous and nonaqueous carriers, diluents, solvents or vehicles include water, ethanol, polyols (propylene glycol, polyethylene glycol, glycerol, and the like), suitable mixtures thereof, vegetable oils (such as olive oil) and injectable organic esters such as ethyl oleate. Proper fluidity may be maintained, for example, by the use of a coating such as lecithin, by the maintenance of the required particle size in the case of dispersions, and by the use of surfactants.

These compositions may also contain adjuvants such as preserving, wetting, emulsifying, and dispersing agents. Prevention of the action of microorganisms may be ensured by various antibacterial and antifungal agents, for example, parabens, chlorobutanol, phenol, sorbic acid, and the like. It may also be desirable to include isotonic agents, for example, sugars, sodium chloride and the like. Prolonged absorption of the injectable pharmaceutical form may be brought about by the use of agents delaying absorption, for example, aluminum monostearate and gelatin.

If desired, and for more effective distribution, the compounds may be incorporated into slow-release or targeted-delivery systems, such as polymer matrices, liposomes, and microspheres. They may be sterilized, for example, by filtration through a bacteria-retaining filter, or by incorporating sterilizing agents in the form of sterile solid compositions, which may be dissolved in sterile water, or some other sterile injectable medium immediately before use.

Solid dosage forms for oral administration may include capsules, tablets, pills, powders, and granules. In such solid dosage forms, the active compound is admixed with at least one inert customary excipient (or carrier), such as sodium citrate or dicalcium phosphate, and additionally (a) fillers or extenders, as for example, starches, lactose, sucrose, glucose, mannitol and silicic acid; (b) binders, as for example, carboxymethylcellulose, alginates, gelatin, polyvinylpyrrolidone, sucrose and acacia; (c) humectants, as for example, glycerol; (d) disintegrating agents, as for example, agar-agar, calcium carbonate, potato or tapioca starch, alginic acid, certain complex silicates and sodium carbonate; (e) solution retarders, as for example paraffin; (f) absorption accelerators, as for example, quaternary ammonium compounds; (g) wetting agents, as for example, cetyl alcohol and glycerol monostearate; (h) adsorbents, as for example, kaolin and bentonite; and (i) lubricants, as for example, talc, calcium stearate, magnesium stearate, solid polyethylene glycols, sodium lauryl sulfate or mixtures thereof. In the case of capsules, tablets and pills, the dosage forms may also comprise buffering agents.

Solid compositions of a similar type may also be employed as fillers in soft and hard-filled gelatin capsules, using such excipients as lactose or milk sugar, as well as high molecular weight polyethylene glycols, and the like.

Solid dosage forms such as tablets, dragees, capsules, pills and granules may be prepared with coatings and shells, such as enteric coatings and others well known in this art. They may contain pacifying agents, and may also be of such composition that they release the active compound or compounds in a certain part of the intestinal tract in a delayed manner. Examples of embedding compositions which may be used are polymeric substances and waxes.

The active compounds may also be in micro-encapsulated form, if appropriate, with one or more of the above-mentioned excipients.

Liquid dosage forms for oral administration include pharmaceutically acceptable emulsions, solutions, suspensions, syrups and elixirs. In addition to the active compounds, the liquid dosage forms may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils, in particular, cottonseed oil, groundnut oil, corn germ oil, olive oil, castor oil and sesame oil, glycerol, tetrahydrofurfuryl alcohol, polyethylene glycols and fatty acid esters of sorbitan or mixtures of these substances, and the like.

Besides such inert diluents, these liquid dosage forms may also include adjuvants, such as wetting agents, emulsifying and suspending agents, sweetening, flavoring and perfuming agents.

Suspensions, in addition to the active compounds, may contain suspending agents, as for example, ethoxylated isostearyl alcohols, polyoxyethylene sorbitol and sorbitan esters, microcrystalline cellulose, aluminum metahydroxide, bentonite, agar-agar and tragacanth, or mixtures of these substances, and the like.

Compositions for rectal or vaginal administrations are preferably suppositories which can be prepared by mixing the compounds of this invention with suitable nonirritating excipients or carriers such as cocoa butter, polyethylene glycol or a suppository wax, which are solid at ordinary temperatures but liquid at body temperature and therefore, melt in the rectum or vaginal cavity and release the active component.

Dosage forms for topical or transdermal administration of a compound of this invention further include ointments, pastes, creams, lotions, gels, powders, solutions, sprays, inhalants or transdermal patches. Transdermal administration via a transdermal patch is a particularly effective and preferred dosage form of the present invention. The active component is admixed under sterile conditions with a pharmaceutically acceptable carrier and any needed preservative, buffers or propellants as may be required. It is known that some agents may require special handling in the preparation of transdermal patch formulations. For example, compounds that are volatile in nature may require admixture with special formulating agents or with special packaging materials to assure proper dosage delivery. In addition, compounds which are very rapidly absorbed through the skin may require formulation with absorption-retarding agents or barriers. Ophthalmic formulations, eye ointments, powders and solutions are also contemplated as being within the scope of this invention.

The present compounds may also be administered in the form of liposomes. As is known in the art, liposomes are generally derived from phospholipids or other lipid substances. Liposomes are formed by mono- or multi-lamellar hydrated liquid crystals that are dispersed in an aqueous medium. Any non-toxic, physiologically acceptable and metabolizable lipid capable of forming liposomes may be used. The present compositions in liposome form may contain, in addition to the compounds of the present invention, stabilizers, preservatives, excipients, and the like. The preferred lipids are the phospholipids and the phosphatidylcholines (lecithins), both natural and synthetic. Methods to form liposomes are known in the art. See, for example, Prescott, Ed., *Methods in Cell Biology*, Volume XIV, Academic Press, New York, N.Y., (1976), p 33 et seq.

In order to reduce unwanted peripherally mediated side-effects, it is advantageous, but not essential, to incorporate into the composition a peripherally acting anti-cholinergic such as N-methylscopolamine, N-methylatropine, propantheline, methantheline, or glycopyrrolate.

Synthetic Methods

The compounds of the present invention may be synthesized as shown in reaction schemes I and II presented below using the reactions and techniques described in this section. The reactions are performed in a solvent appropriate to the reagents and materials employed are suitable for the transformation being effected. It is understood by those skilled in the art of organic synthesis that the functionality present on the heterocyclic ring and other portions of the molecule must be consistent with the chemical transformation proposed. This will, on occasion, necessitate judgment by the routineer as to the order of synthetic steps, protecting groups required, and deprotection conditions. Substituents on the starting materials may be incompatible with some of the reaction conditions required in some of the methods described, but alternative methods and substituents compatible with the reaction conditions will be readily apparent to skilled practitioners in the art. The use of nitrogen-protecting groups is well known in the art for protecting amino groups against undesirable reactions during a synthetic procedure and many such protecting groups are known, cf., for example, T. H. Greene and P. G. M. Wuts, *Protective Groups in Organic Synthesis*, 2nd edition, John Wiley & Sons, New York (1991).

Scheme 1

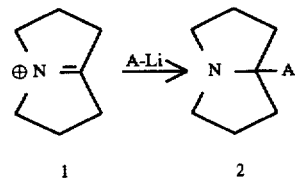

1          2

In accordance with Scheme 1 are prepared compounds of Formula (I) wherein A is selected from options (c)–(g), as described above. A compound A—X, wherein A is selected from options (c)–(g), as described above and wherein X is I or Br, is treated with an alkyl lithium, for example, n-butyllithium or t-butyllithium, at a temperature of about −100° C. to −28° C., to give an A—Li compound, for example,

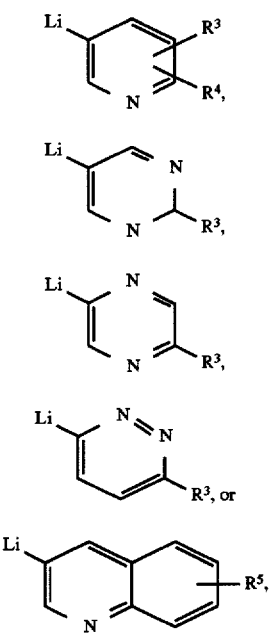

wherein $R^3$, $R^4$ and $R^5$ are as defined previously for compounds of Formula (I). The A—Li compound is reacted with compound (1), a starting material prepared according to the procedure of Miyano et al. (Synthesis, 701 (1978)), beginning the reaction at a temperature of from −100° C. to −70° C. and warming to a temperature from −30° C. to ambient, in a suitable solvent, such as ether or THF, for example, for a period of from 0.2 to 24 hours to give the desired compounds (2), which are specific exemplars of Formula (I) above. Alternately, when $R^3$, $R^4$ or $R^5$ is F, Cl or Br, particularly when substituted at a ring position adjacent to a ring nitrogen atom, either may be displaced by another nucleophile, for example, a different halogen, ammonia or an amine, a $C_1$-$C_8$-alkoxide, or a $C_1$-$C_8$ thiolate to give additional compounds of Formula (I) above. A primary amino group can be further modified by acylation with suitably activated carboxylic, carbonic, or carbamic acid, or by conversion to hydroxy using a diazotization/hydrolysis sequence, or to halo, by a diazotization/halide displacement, e.g. under well-known Sandmeyer conditions, or to nitro by oxidation, for example with hydrogen peroxide in sulfuric acid.

Scheme 2

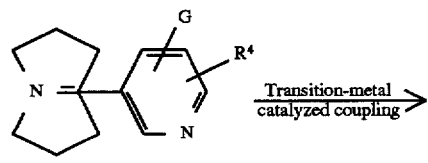

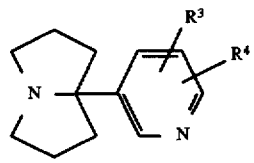

Alternately, as illustrated in Scheme 2, $R^3$ or $R^4$ may be a group G, where G is a sulfonate, for example O—$SO_2CF_3$, or halo, particularly bromo or iodo, which is replaceable by a variety of functional groups with the aid of transition metal catalysis using methods well known to those skilled in the art. Thus, reaction of compound (3) with $Zn(CN)_2$ with the aid of palladium catalysis and heat and a suitable solvent such as DMF or N-methylpyrrolidinone provides compounds I ($R_3$=CN). Moreover, using well-established methods, the cyano group can be further transformed, for example reduction (to —$CH_2NH_2$), or by hydrolysis (to $CO_2H$), or by reaction with any of a variety of organometallic agent followed by hydrolysis (to give ketones), or by cycloaddition of 1,3-dipolarophiles (to give heterocycles). The —$CH_2NH_2$ group can be further modified by alkylation with an alkyl halide, or alternately by reaction with an aldehyde or ketone under reducing conditions, or by acylation with a suitably activated carboxylic, carbonic, or carbamic acid.

Alternately, replacement of G with aryl, substituted aryl, heteroaryl or substituted heteroaryl can be accomplished by reaction of (3) with the appropriate aryl- or heteroarylboronic acid under palladium catalysis in a suitable solvent such as benzene, toluene, DMF, THF, or the like, at temperatures of about 40° C. to 120° C. Replacement of G with alkenyl, substituted alkenyl, dienyl or substituted dienyl can be accomplished by reaction of (3) with the appropriate alkene or diene under Heck conditions, i.e. under palladium catalysis in a suitable solvent such as benzene, toluene, DMF, THF, or the like, at temperatures of about 40° C. to 120° C. Replacement of G with alkynyl or substituted alkynyl can be accomplished by reaction of (3) with the appropriate alkyne or substituted alkyne under palladium catalysis in the presence of a Cu (I) salt and a base such as a tertiary amine, for example triethylamine, in a suitable solvent such as benzene, toluene, DMF, THF, or the like, at temperatures of about 40° C. to 120° C. Alkenes or alkynes obtained as described above, can be reduced to alkanes by appropriate hydrogenation techniques, such as treatment with hydrogen over a noble metal catalyst.

Scheme 3

$R^1$—CH2—$NO_2$ + Ph—NCO ⟶ $R^1.C \equiv \overset{\oplus}{N} — \overset{\ominus}{O}$ 4     5     6

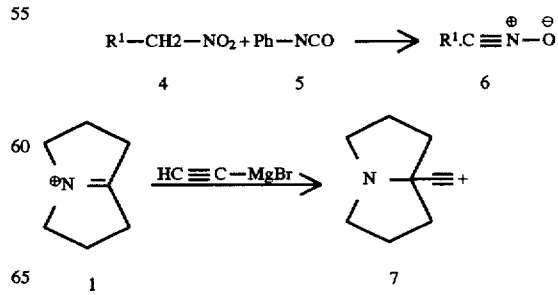

-continued
Scheme 3

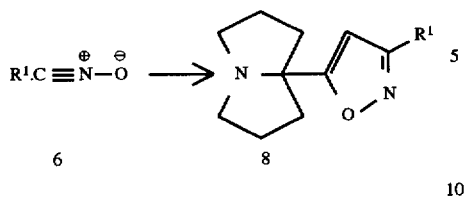

In accordance with Scheme 3 are prepared compounds of Formula (I) wherein A is selected from option (a) described above. Compound (7) is first prepared from compound (1) by treatment with ethynylmagnesium bromide under the conditions described for Scheme 1 above. In the presence of the acetylene compound (7), nitrile-oxide compound (6) is generated from a nitro compound (4), wherein $R^1$ is as described previously, by reaction with phenylisocyanate (5) in benzene or toluene, for example, at from 60° C. to the reflux temperature of the solvent for to 6 to 24 hours, and compounds (6) and (7) react to give the desired isoxazolyl compound (8), which also is a specific exemplar of Formula (I).

In accordance with Scheme 4 below are prepared compounds of Formula (I) wherein A is selected from options (a) and (b) above wherein $R^1$ is methyl. A protected proline carboxylic ester (9) is reacted with LDA at −78° to 0° C. and then with allyl bromide at a temperature from −78° C. to ambient to give the allyl substituted pyrrolidine compound (10). Compound (10) is selectively hydrated at the terminal carbon atom by sequential treatment with $BH_3$ and $H_2O_2$. The alcohol intermediate is then mesylated by treatment with methanesulfonyl chloride in the presence of base to give compound (11). Compound (1) is deprotected by standard methods, such as removal of carbobenzoxy with hydrogen in the presence of palladium catalyst, for example, which also induces cyclization to afford the bicyclic compound (12). Compound (12) is then treated with the dilithio anion of acetone oxime (of course,other oximes can be produced from the corresponding ketone to vary $R^1$ accordingly), and the intermediate compound is cyclized by treatment with dehydrating conditions, such as $H_2SO_4$, to give compound (13), also a representative example of Formula (1). Alternately, compound 12 is treated with the dilithio anion of acetone oxime, then treated with an appropriately substituted hydrazine to give the compound (14), wherein $R^2$ is as described for compounds of Formula (I) previously, which is also a representative example of Formula (I).

Scheme 4

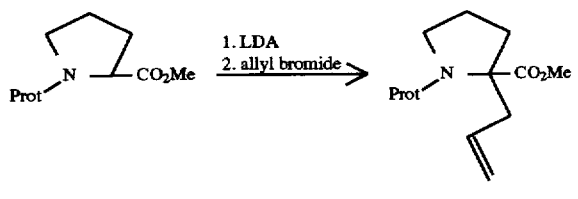

-continued
Scheme 4

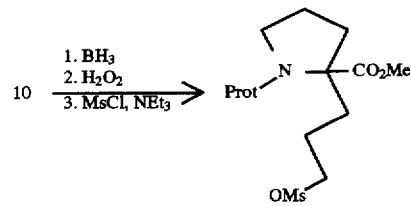

A. Protocol For Determination of Nicotinic Acetylcholine Receptor Binding Potencies of Ligands For the purpose of identifying compounds as cholinergic agents which are capable of interacting with nicotinic acetylcholine receptors in the brain, a ligand-receptor binding assay was carried out as the initial screen. Compounds of the present invention were effective at interacting with neuronal nicotinic acetylcholine receptors as assayed for their ability to displace radioligand from neuronal nicotinic acetylcholine channel receptors labeled with [$^3$H]-cytisine ([$^3$H]-CYT).

Displacement of [$^3$H]-CYT from nicotinic acetylcholine receptors was determined using crude synaptic membrane preparations from whole rat brain (Pabreza et al., *Molecular Pharmacol.*, 1990, 39: 9). Washed membranes were stored at −80° C. prior to use. Frozen aliquots were slowly thawed and resuspended in 20 volumes of buffer (containing: 120 mM NaCl, 5 mM KCl, 2 mM MgCl$_2$, 2 mM CaCl$_2$ and 50 mM Tris-Cl, pH 7.4 @4° C.). After centrifuging at 20,000×g for 15 minutes, the pellets were resuspended in 30 volumes of buffer. Homogenate (containing 125–150 µg protein) was added to triplicate tubes containing concentrations of test compound and [$^3$H]-CYT (1.25 nM) in a final volume of 500 µL. Samples were incubated for 60 minutes at 4° C., then rapidly filtered through Whatman GF/B filters presoaked in 0.5% polyethylimine using 3×4 mL of ice-cold buffer. The filters are counted in 4 mL of Ecolume® (ICN). Nonspecific binding was determined in the presence of 10 µM (−)-nicotine and values were expressed as a percentage of total binding. IC$_{50}$ values were determined with the RS-1 (BBN) nonlinear least squares curve-fitting program and IC$_{50}$ values were converted to Ki values using the Cheng and Prusoff correction (Ki=IC$_{50}$/(1+[ligand]/Kd of ligand). Alternately, data were expressed as a percentage of the total specific binding. The results (shown in Table 1) suggest that the compounds of the present invention have high affinity for the neuronal nicotinic acetylcholine receptor.

B. Protocols for the Determination of Functional Effects of Nicotinic Acetylcholine Receptor Ligands on Synaptic Transmission The ability of the compounds of the invention to interact with neuronal nicotinic acetylcholine receptors and thereby to activate or inhibit synaptic transmission can be demonstrated in vitro using the following protocol. Cells of the IMR-32 human neuroblastoma clonal cell line (ATCC, Rockville, Md.) were maintained in a log phase of growth according to established procedures (Lukas, 1993). Experimental cells were seeded at a density of 500,000 cells/mL into a 24-well tissue culture dish. Plated cells were allowed to proliferate for at least 48 hours before loading with 2 µCi/mL of $^{86}$Rb$^+$ (35 Ci/mmol) overnight at 37° C. The $^{86}$Rb$^+$ efflux assays were performed according to previously published protocols (Lukas, R. J., *J. Pharmacol. Exp. Ther.*, 265: 294–302, 1993) except serum-free Dulbecco's Modified Eagle's Medium was used during the $^{86}$Rb$^+$ loading, rinsing, and agonist-induced efflux steps.

Responses (reported as percent relative to the response elicited by 100 µM (S)-nicotine) are shown for the indicated concentrations of selected compounds of the invention. The inhibition data (given for other selected compounds) reflect inhibition of the efflux elicited by 100 µM (S)-nicotine at the indicated concentration. The results (also shown in Table 1) suggest that selected compounds of the present invention either activate or inhibit the initial ion flux aspects of synaptic transmission mediated by neuronal nicotinic acetylcholine receptors. This finding is in agreement with the results of others who have linked dopamine release, which is dependent upon the ion flux in synaptic transmission, to binding at nicotinic receptors (cf., for example, Lippiello and Caldwell, U.S. Pat. No. 5,242,935, issued Sep. 7, 1993; Caldwell and Lippiello, U.S. Pat. No. 5,248,690, issued Sep. 28, 1993; and Wonnacott et al., Prog. Brain Res., 79: 157–163 (1989)).

TABLE 1

Binding to Neuronal Nicotinic Acetylcholine Receptors and Activation or Inhibition of Neuronal Nicotinic Acetylcholine Receptors in IMR-32 Cells

| Ex. No | Binding (nM) | IMR-32 % response (conc.) | IMR-32 % Inhibition (conc.) |
|---|---|---|---|
| 1 | 0.97 | 110 (10 µM) | |
| 2 | 70 | | |
| 3 | 0.38 | 71 (10 µM) | |
| 4 | 4.3 | 40 (10 µM) | |
| 5 | 0.10 | 82 (1 µM) | |
| 6 | 5.7 | | |
| 7 | 436 | | |
| 8 | 0.055 | 71 (1 µM) | |
| 9 | 3.7 | 39 (100 µM) | |
| 10 | 2.9 | 13 (10 µM) | 12 (10 µM) |
| 11 | 1417 | | |
| 12 | 0.27 | 93 (10 µM)) | |
| 13 | 1.4 | 108 (100 µM) | |
| 14 | 1.7 | 74 (100 µM) | |
| 15 | 4.0 | | |
| 16 | 1.4 | 53 (100 µM) | |
| 16b | 0.27 | | |
| 17 | 0.61 | 41 (10 µM) | |
| 18 | 0.11 | 66 (10 µM) | |
| 19 | 0.05 | 91 (1 µM) | |
| 20 | 0.56 | 98 (1 µM) | |
| 21 | 0.33 | 56 (1 µM) | |
| 22 | 0.22 | 42 (10 µM) | |
| 23 | 0.23 | 68 (10 µM) | |
| 24 | 72 | 0 (100 µM) | 14 (10 µM) |
| 25 | 0.25 | | |

In addition, the compounds of the invention are useful as binders to the α$_7$-nicotinic acetylcholine receptor, which is one indicator of utility for treating certain forms of psychosis, for treating certain forms of cognitive deficits, or as neuroprotective agents. The compounds (1–14, 16b, 19, 20, 21 and 25) exhibited a binding affinity relative to the known alpha$_7$ binder bungarotoxin of between 0.9–16.200 nM. The compounds, therefore, bind to several nicotinic receptor subtypes. The present invention is therefore directed to a compound of formula I or a pharmaceutical composition thereof which binds to both the alpha4beta2 receptor and to the alpha 7 receptor in mammals including humans and to a method of binding to either or both nicotinic receptor subtypes comprising administering a pharmaceutically effective amount of said compound or salt thereof in an in vitro or in vivo screen or to a patient in need of treatment thereof.

EXAMPLES

The following examples will serve to further illustrate preparation of the novel compounds of the invention and their biological activity. They are not to be read as limiting the scope of the invention as it is defined by the appended claims.

Thin-layer chromatography (TLC) was performed on 0.25 mm E. Merck precoated silica gel plates (60 F-254). Flash chromatography was performed on 200–400 mesh silica gel (E. Merck), and column chromatography was performed on 70–230 mesh silica gel (E. Merck).

The following abbreviations are used: THF for tetrahydrofuran, DMF for N, N-dimethylformamide, D$_2$O for deuterium oxide, CDCl$_3$ for deuterochloroform, DMSO-$_6$ for deuterodimethylsulfoxide, BOC for tert-butyloxycarbonyl, CBZ for benzyloxycarbonyl, Bn for benzyl, Ms for methanesulfonyl, PAW for pyridine/acetic acid/water (20:6:11), DCC for dicyclohexylcarbodiimide, DIBALH for diisobutylaluminum hydride, DIEA for diisopropylethylamine, DME for 1,2-dimethoxyethane, DMSO for dimethylsulfoxide; DPPA for diphenylphosphoroyl azide, EDCI for 1-(3-dimethyl-aminopropyl)-3-ethylcarbodiimide hydrochloride, EtOAc for ethyl acetate; EtOH for ethanol, Et$_2$O for diethyl ether; IBCF for isobutyl chloroformate, HOAc for acetic acid, HOBT for 1-hydroxybenzotriazole, LAH for lithium aluminum hydride, NH$_4$OAc for ammonium acetate, dppp for 1,3-bis (diphenylphosphino)propane; NMM for N-methylmorpholine, TEA for triethylamine, THF for tetrahydrofuran.

Example 1

7a-(3-methyl-5-isoxazolyl)-hexahydro-1H-pyrrolizine hydrochloride 1a. 1-Benzyloxycarbonyl-2-(methoxycarbonyl)-2-(2-propenyl)pyrrolidine Under a nitrogen atmosphere, diisopropylamine (16.4 mL, 117.2 mmol) was dissolved in THF (117 mL) and cooled to −78° C. A 2.5M solution of n-butyllithium in hexane (43 mL, 107.5 mmol) was then added dropwise followed by stirring for 15 minutes and then 1-benzyloxycarbonylproline methyl ester (25.7 g, 97.7 mmol) in THF (575 mL) was added to the reaction vessel dropwise over a 40 minute period. The reaction mixture was allowed to stir for 15 minutes at −78° C., neat allyl bromide (25.4 mL, 293 mmol) was added at a steady rate followed with stirring for 15 minutes at −78° C. and for an additional 2 hours at between −35° C. and −25° C. A phosphate buffer solution (~100 mL), pH=7, was next poured into the reaction vessel and the reaction mixture was allowed to warm to ambient temperature. The mixture was diluted with EtOAc, washed in succession with 2N HCl and brine, dried (Na$_2$SO$_4$) and concentrated. The residue was chromatographed (silica gel; EtOAc/hexane 1:20 to 1:15 to 1:10) to afford a yellow oil (17.8 g, 63%). R$_f$ 0.31 (EtOAc/hexane, 1:4). MS (CI/NH$_3$) m/e: 304 (M+H)$^+$. $^1$H NMR (DMSO-d$_6$, 300 MHz) δ1.77–1.86 (m, 2H), 1.94–2.13 (m, 2H), 2.50–2.59 (m, 1H partially buried under DMSO), 2.84 minor conformer and 2.92 major conformer (dd, J=14.0 Hz, 7.0 Hz, 1H), 3.28–3.62 (m, 5H), 4.96–5.11 (m, 4H), 5.64–5.75 (m, 1H), 7.27–7.41 (m, 5H).

1b. 1-Benzyloxycarbonyl-2-(3-hydroxypropyl)-2-(methoxycarbonyl) pyrrolidine

1-Benzyloxycarbonyl-2-(methoxycarbonyl)-2-(2-propenyl) pyrrolidine (from step 1a, 21.0 g, 69.4 mmol) was dissolved in THF (70 mL) and 1.0M borane THF complex (45 mL, 45 mmol) was added dropwise to the reaction vessel over a 40 minute period. The reaction mixture was allowed to stir for one hour, then ~10 mL of water was carefully added followed by the successive addition of 3N NaOH (16.2 mL, 48.5 mmol) and 30% hydrogen peroxide (5.5 mL, 48.5 mmol). The mixture was allowed to stir for one hour then was poured into a separatory funnel containing 250 mL of water and 15 mL 10% Na$_2$S$_2$O$_3$. The aqueous solution was extracted with CH$_2$Cl$_2$ (3×) and the organic fractions combined, washed in succession with saturated NaHCO$_3$ and then brine, dried (Na$_2$SO$_4$) and concentrated. The residue was chromatographed (silica gel; EtOAc/hexane, 1:4 to 1:2 to 1:1 to EtOAc) to afford a clear viscous oil (12.3 g, 55% yield). R$_f$ 0.18 (EtOAc/hexane, 1:1). MS (CI/NH$_3$) m/e: 322 (M+H)$^+$. $^1$H NMR (CDCl$_3$, 300 MHz) δ1.20–2.41 (m, 8H), 3.45–3.82 (m, 7H), 5.06–5.18 (m, 2H), 7.29–7.37 (m, 5H).

1c. 1-Benzyloxycarbonyl-2-(methoxycarbonyl-2-(3-methylsulfonyloxy-propyl)pyrrolidine 1-Benzyloxycarbonyl-2-(3-hydroxypropyl)-2-(methoxycarbonyl) pyrrolidine (from step 1b, 10.7 g, 33.2 mmol) and triethylamine (4.9 mL, 34.9 mmol) were combined in THF (133 mL) and cooled to 0° C. under a nitrogen atmosphere. Methanesulfonyl chloride (2.70 mL, 34.9 mmol) was added dropwise to the reaction mixture and stirred for 30 minutes at 0° C. Water was added and the reaction vessel contents were poured into a separatory funnel. The mixture was washed in succession with 10% citric acid solution and then saturated NaHCO$_3$ solution, dried (Na$_2$SO$_4$), concentrated, and the residue chromatographed (silica gel; EtOAc/hexane, 1:1 to 1:2) to afford a clear oil (11.0 g, 83%). R$_f$ 0.25 EtOAc/hexane, 1:1). MS (CI/NH$_3$) m/e: 400 (M+H)$^+$. $^1$H NMR (CDCl$_3$, 300 MHz) δ1.59–2.35 (m, 8H), 2.93 minor conformer and 2.99 major conformer (s, 3H), 3.46–3.80 (m, 5H), 4.07–4.27 (m, 2H), 5.05–5.17 (m, 2H), 7.29–7.36 (m, 5H).

1d. 7a-(Methoxycarbonyl)-hexahydro-1H-pyrrolizine

1-Benzyloxycarbonyl-2-(methoxycarbonyl)-2-(3-methylsulfonyloxypropyl)pyrrolidine (from step 1c, 11.0 g, 27.6 mmol) was dissolved in MeOH and exposed to hydrogen gas at a pressure of 4 atmospheres in the presence of 10% palladium on carbon (11.0 g) for 48 hours. The reaction was filtered and the filtrate evaporated. The crude was chromatographed (silica gel; CHCl$_3$/MeOH, 98:2 to 95:5 to 90:10) to afford a yellow oil (4.23 g, 90%). R$_f$ 0.53 (CHCl$_3$/MeOH, 90:10). MS (CI/NH$_3$) m/e: 170 (M+H)$^+$. $^1$H NMR (CDCl$_3$, 300 MHz) δ1.24–1.85 (m, 6H), 2.30 ("qt", J=6.0 Hz, 2H) 2.72 (ddd, J=9.9 Hz, 6.6 Hz, 6.6 Hz, 2H), 3.23 (ddd, J=9.9 Hz, 5.9 Hz, 5.9 Hz, 2H), 3.72 (s, 3H).

1e. 7a-(3-methyl-5-isoxazolyl)-hexahydro-1H-pyrrolizine 8-(Methoxycarbonyl)-hexahydro-1H-pyrrolizine (from step 1d, 1.56 g, 9.22 mmol), acetone oxime (1.45 g, 19.8 mmol) and n-butyllithium (2.5M in hexane, 16 mL, 39.6 mmol) were combined in a similar fashion as that outlined by J. Saunders et at., *J. Med. Chem.* 1990, 33: 1128. The crude material was chromatographed (silica gel; CHCl$_3$/MeOH, 99:1) to afford a yellow oil (199 mg, 11%). MS (CI/NH$_3$) m/e: 193 (M+H)$^+$. $^1$H NMR (CDCl$_3$, 300 MHz) δ1.76–1.92 (m, 6H), 2.14–2.29 (m, 2H), 2.24 (s, 3H), 2.61–2.69 (m, 2H), 3.13–3.32 (m, 2H), 5.95 (s, 1H).

1f. 7a-(3-methyl-5-isoxazolyl)-hexahydro-1H-pyrrolizine hydrochloride 7a-(3-methyl-5-isoxazolyl)-hexahydro-1H-pyrrolizine (from step 1e, 189 mg, 0.98 mmol) was immersed in Et$_2$O (7 mL) and cooled to 0° C. A solution of Et$_2$O saturated with HCl (g) was added to the reaction vessel dropwise with stirring. The solvent was carefully removed and the remaining white solid triturated with Et$_2$O (2×) followed by recrystallization out of MeOH/Et$_2$O (126.5 mg, 56%). mp 169°–171° C. MS (CI/NH$_3$) m/e: 193 (M+H)$^+$. $^1$H NMR (D$_2$O, 300 MHz) δ2.20–2.41 (m, 9H), 2.60–2.68 (m, 2H), 3.31–3.39 (m, 2H), 3.71–3.79 (m, 2H), 6.59 (s, 1H). Anal. Calcd for C$_{11}$H$_{17}$ClN$_2$O: C, 57.76; H, 7.49; N, 12.25. Found: C, 57.84; H, 7.34; N, 12.13.

Example 2

7a-(1H-3-methyl-5-pyrazolyl)-hexahydro-1H-pyrrolizine dihydrochloride 2a. 7a-(1-(1,3-butanedione-3-oxime))-hexahydro-1H-pyrrolizine Butyllithium (1.6M/hexane, 6.2 mL, 9.88 mmol) was added to a solution of acetone oxime (365 mg, 4.9 mmol) in THF (7.5 mL) previously cooled to 0° C. After ten minutes of stirring, 8-(methoxycarbonyl)-hexahydro-1H-pyrrolizine (from Example 1d, 645 mg, 3.8 mmol) in THF (7.6 mL) was added and the reaction mixture allowed to warm to ambient temperature and stir an additional 18 hours. Saturated NH$_4$Cl solution was added, and the phases were separated. Solid K$_2$CO$_3$ was added to the aqueous phase followed by extraction with CHCl$_3$ (3×). The organics were combined, dried (MgSO$_4$), concentrated and the crude product chromatographed (silica gel; CHCl$_3$/MeOH, 90:10) to afford an amber solid (257 mg, 32%). MS (CI/NH$_3$) m/e: 211 (M+H)$^+$.

2a. 7a-(1H-3-methyl-5-pyrazolyl)-hexahydro-1H-pyrrolizine

Ethanol (2.0 mL) saturated with HCl (g) was added to a solution of the above 7a-[1-(1,3-butanedione-3-oxime)]hexahydro-1H-pyrrolizine (from step 2a, 245 mg, 1.16 mmol) and hydrazine (182 µL, 5.80 mmol) in EtOH (2.5 mL). The reaction mixture was heated at reflux for 3 hours and then allowed to cool to ambient temperature. Saturated NH$_4$Cl was added and the phases separated. Solid K$_2$CO$_3$ was added and the aqueous mixture extracted with CHCl$_3$. The organic fraction was dried (MgSO$_4$), concentrated and chromatographed (CHCl$_3$/MeOH/NH$_4$OH, 90:10:0 to 90:9.5:0.5) to afford a solid (97 mg, 44%). mp 56°–58° C. MS (CI/NH$_3$) m/e: 192 (M+H)$^+$. $^1$H NMR (CDCl$_3$, 300 MHz) δ1.72–1.97 (m, 6H), 2.02–2.12 (m, 2H), 2.26 (s, 3H), 2.61–2.71 (m, 2H), 3.18–3.26 (m, 2H), 5.82 (s, 1H).

2c. 7a-(1H-3-methyl-5-pyrazolyl)-hexahydro-1H-pyrrolizine dihydrochloride salt 7a-(1H-3-methyl-5-pyrazolyl)-hexahydro-1H-pyrrolizine (from step 2b, 90.0 mg, 0.47 mmol) was dissolved in THF:MeOH (10:1, 11 mL) and Et$_2$O saturated with HCl (g) was added dropwise. The solvent was removed and the remaining solid triturated with Et$_2$O (2×) and then recrystallized from MeOH/Et$_2$O to afford a crystalline white solid (90.0 mg, 72%). mp 130°–132° C. MS (CI/NH$_3$) m/e: 192 (M+H)$^+$. $^1$H NMR (D$_2$O, 300 MHz) δ2.08–2.33 (m, 9H), 2.50–2.59 (m, 2H), 3.22–3.31 (m, 2H), 3.65–3.74 (m, 2H), 6.27 (s, 1H). Anal. Calcd for C$_{11}$H$_{18}$Cl$_2$N$_3$: C, 50.01; H, 7.25; N, 15.90. Found: C, 49.71; H, 7.49; N, 15.77.

Example 3

7a-(3-pyridinyl)-hexahydro-1H-pyrrolizine hydrochloride 3a. 7a-(3-pyridinyl)-hexahydro-1H-pyrrolizine A solution of 2.5M n-butyllithium in hexanes (2.9 mL, 7.2 mmol) was added dropwise to a solution of 3-bromopyridine (0.690 mL, 7.2 mmol) in Et$_2$O (10 mL) at −78° C. After stirring for 10 minutes, 1,2,3,5,6,7-hexahydropyrrolizinium perchlorate (500 mg, 2.4 mmol), prepared according to S. Miyano et al., *Synthesis* 1978, 701–702 and S. Miyano et al., *Journal of Heterocyclic Chemistry*, 1982, 19:1465–1468, was introduced into the reaction vessel followed by stirring at −78° C. for 4 hours. The reaction mixture was allowed to warm to ambient temperature, and 2N HCl was added. The phases were separated, and the aqueous phase was basified with 15% NaOH solution and extracted with CHCl$_3$ (3×). The organic fractions were combined, dried (MgSO$_4$), concentrated and chromatographed (silica gel; CHCl$_3$/MeOH, 97.5:2.5) to afford an amber oil (260 mg, 58%). R$_f$=0.2 (CHCl$_3$/MeOH, 90:10). MS (CI/NH$_3$) m/e: 189 (M+H)$^+$. $^1$H NMR (CDCl$_3$, 300 MHz) δ1.58–1.76 (m, 2H), 1.79–1.90 (m, 2H), 1.92–2.08 (m, 4H), 2.66–2.74 (m, 2H), 3.13–3.20 (m, 2H), 7.19 (dd, J=7.7, 4.8 Hz, 1H), 7.82 (ddd, J=7.7, 2.6, 1.4 Hz, 1H), 8.41 (dd, J=4.8, 1.4 Hz, 1H), 8.71 (d, J=2.6 Hz, 1H).

3b. 7a-(3-pyridinyl)-hexahydro-1H-pyrrolizine hydrochloride salt 7a-(3-pyridinyl)-hexahydro-1H-pyrrolizine (from step 3a, 125 mg, 0.66 mmol) was dissolved in CH$_2$Cl$_2$ (15 mL) and Et$_2$O saturated with HCl (g) was added dropwise. The solvent was removed, and the remaining solid was triturated with CH$_2$Cl$_2$ (2×) to afford a hygroscopic yellow solid (140 mg, 81%). MS (CI/NH$_3$) m/e: 189 (M+H)$^+$. $^1$H NMR (D$_2$O, 300 MHz) δ2.13–2.29 (m, 2H), 2.32–2.43 (m, 2H), 2.48–2.69 (m, 4H), 3.40–3.49 (m, 2H), 3.83–3.92 (m, 2H), 7.92 (dd, J=8.5, 5.5 Hz, 1H), 8.43 (ddd, J=8.5, 2.6, 1.4 Hz, 1H), 8.75 (dd, J=5.5, 1.4 Hz, 1H), 8.88 (d, J=2.6 Hz, 1H). Anal. Calcd for C$_{12}$H$_{18}$Cl$_2$N$_2$.0.5H$_2$O: C, 53.34; H, 7.09; N, 10.37. Found: C, 53.28; H, 6.96; N, 10.22.

Example 4

7a-(3-quinolinyl)-hexahydro-1H-pyrrolizine dihydrochloride 4a. 7a-(3-quinolinyl)-hexahydro-1H-pyrrolizine A solution of 2.5M nBuLi (1.2 mL, 2.8 mmol) in hexanes was added to 3-bromoquinoline (386 µL, 2.8 mmol) in THF (10 mL) at −100° C. followed immediately by 1,2,3,5,6,7-hexahydropyrrolizinium perchlorate (200 mg, 0.9 mmol). The reaction mixture was allowed to stir for 2 hours at −100° C. and then 2N HCl was added at 0° C. After warming to ambient temperature, the mixture was poured over EtOAc and the phases were separated. The aqueous phase was basified with 15% NaOH solution and extracted with CH$_2$Cl$_2$ (3×). The organic fractions were combined, dried (MgSO$_4$) and concentrated, and the residue was chromatographed (silica gel; EtOAc) to afford a pale solid (104 mg, 46%). mp 80°–83° C. MS (CI/NH$_3$) m/e: 239 (M+H)$^+$. $^1$H NMR (CDCl$_3$, 300 MHz) δ1.61–1.75 (m, 2H), 1.83–1.94 (m, 2H), 2.03–2.17 (m, 4H), 2.71–2.80 (m, 2H), 3.20–3.27 (m, 2H), 7.52 (ddd, J=7.0, 7.0, 1.1 Hz, 1H), 7.65 (ddd, J=7.0, 7.0, 1.5 Hz, 1H), 7.82 (d, J=8.1 Hz, 1H), 8.05 (d, J=8.5 Hz, 1H), 8.32 (d, J=2.2, Hz, 1H), 8.97 (d, J=2.2 Hz, 1H).

4b. 7a-(3-quinolinyl)-hexahydro-1H-pyrrolizine dihydrochloride salt 7a-(3-Quinolinyl)-hexahydro-1H-pyrrolizine (from step 4a, 95 mg, 0.4 mmol) was dissolved in CH$_2$Cl$_2$ (5 mL), and Et$_2$O saturated with HCl(g) was added to the reaction solution. The solvent was removed, and the remaining solid was recrystallized from MeOH/Et$_2$O to afford short white hygroscopic needles (65 mg, 52%). MS (CI/NH$_3$) m/e: 239 (M+H)$^+$. $^1$H NMR (D$_2$O, 300 MHz) δ2.21–2.49 (m, 4H), 2.55–2.64 (m, 2H), 2.72–2.81 (m, 2H), 3.42–3.51 (m, 2H), 3.90–3.98 (m, 2H), 7.87 (ddd, J=7.0, 7.0, 1.1 Hz, 1H), 8.05 (ddd, J=7.0, 7.0, 1.1 Hz, 1H), 8.17 (m, 2H), 8.85 (d, J=2.6 Hz, 1H), 9.13 (d, J=2.6 Hz, 1H). Anal. Calcd for C$_{16}$H$_{20}$Cl$_2$N$_2$.1.4 H$_2$O: C, 57.11; H, 6.83; N, 8.33. Found: C, 57.17; H, 6.90; N, 8.17.

Example 5

7a-(6-chloro-3-pyridinyl)-hexahydro-1H-pyrrolizine hydrochloride 5a. 7a-(6-chloro-3-pyridinyl)-hexahydro-1H-pyrrolizine A 2.5M solution of nBuLi (1.8 mL, 4.4 mmol) in hexanes was added dropwise to 2-chloro-5-iodopyridine (1.0 g, 4.2 mmol, prepared according to S. C. Clayton and A. C. Regan, *Tetrahedron Letters* 1993, 34: 7493–7496), slurried in Et$_2$O (17 mL) at −78° C. After stirring for 15 minutes, 1,2,3,5,6,7-hexahydropyrrolizinium perchlorate (1.0 g, 5.0 mmol) was added, and the reaction mixture was allowed to warm to ambient temperature. A solution of 2N HCl was added, and the phases were separated. The aqueous phase was basified with 15% NaOH solution and extracted with CH$_2$Cl$_2$ (3×). The organic phases were combined, dried (MgSO$_4$) and concentrated, and the residue was chromatographed (silica gel: CHCl$_3$/MeOH, 99:1) to afford a yellow oil (219 mg, 23%). $R_f$=0.2 (CHCl$_3$/MeOH, 98:2). MS (CI/NH$_3$) m/e: 223 (M+H)$^+$. $^1$H NMR (CDCl$_3$, 300 MHz) δ1.58–1.71 (m, 2H), 1.79–2.08 (m, 6H), 2.63–2.71 (m, 2H), 3.11–3.18 (m, 2H), 7.22 (d, J=8.5 Hz, 1H), 7.80 (dd, J=8.5, 2.6 Hz, 1), 8.48 (d, J=2.6 Hz, 1H).

5b. 7a-(6-chloro-3-pyridinyl)-hexahydro-1H-pyrrolizine hydrochloride salt 7a-(6-Chloro-3-pyridinyl)-hexahydro-1H-pyrrolizine (from step 5a, 210 mg, 0.94 mmol) was dissolved in Et$_2$O (8 mL), and Et$_2$O saturated with HCl (g) was added at ambient temperature. Solvent was then removed, and the remaining solid was recrystallized from MeOH/Et$_2$O to afford short white needles (189 mg, 78%). mp 141°–143° C. MS (CI/NH$_3$) m/e: 223 (M+H)$^+$. $^1$H NMR D$_2$O, 300 MHz) δ2.12–2.50 (m, 6H), 2.58–2.65 (m, 2H), 3.33–3.42 (m, 2H), 3.69–3.88 (m, 2H), 7.62 (d, J=8.5 Hz, 1HO, 7.99 (dd, J=8.5, 2.7 Hz, 1H), 8.53 (d, J=2.7 Hz, 1H). Anal. Calcd for C$_{12}$H$_{16}$Cl$_2$N$_2$: C, 55.61; H, 6.22; N, 10.81. Found: C, 55.10; H, 6.36; N, 10.57.

Example 6

7a-(2-fluoro-3-pyridinyl)-hexahydro-1H-pyrrolizine hydrochloride salt 6a. 7a-(2-fluoro-3-pyridinyl)-hexahydro-1H-pyrrolizine A solution of 2.5M nBuLi (680 μL, 1.7 mmol) in hexanes was added to diisopropylamine (220 μL, 1.7 mmol) in THF (4.5 mL) at ambient temperature. After 10 minutes of stirring, the reaction mixture was cooled to −78° C., 2-fluoropyridine was added neat, and stirring was continued for 4 hours at −78° C. 1,2,3,5,6,7-hexahydropyrrolizinium perchlorate (500 mg, 2.4 mmol) was added, and the reaction mixture was allowed to stir for 2 hours at −78° C. then warm to ambient temperature. A solution of 2N HCl was added, and the mixture was then poured over EtOAc. The phases were separated, and the aqueous phase was basified with 15% NaOH and extracted with CH$_2$Cl$_2$ (2×). The CH$_2$Cl$_2$ fractions were combined, dried (MgSO$_4$) and concentrated, and the residue was chromatographed (silica gel; CHCl$_3$/MeOH, 98:2) to afford a clear oil (66 mg, 20%). $R_f$=0.38 (CHCl$_3$/MeOH, 95:5). MS (CI/NH$_3$) m/e: 207 (M+H)$^+$. $^1$H NMR (CDCl$_3$, 300 MHz) δ1.52–1.64 (m, 2H), 1.78–1.89 (m, 2H), 1.97–2.12 (m, 4H), 2.65–2.72 (m, 2H), 3.08–3.14 (m, 2H), 7.08–7.12 (m, 1H), 8.00–8.03 (m, 1H), 8.18–8.24 (m, 1H).

6b. 7a-(2-fluoro-3-pyridinyl)-hexahydro-1H-pyrrolizine hydrochloride salt 7a-(2-fluoro-3-pyridinyl)-hexahydro-1H-pyrrolizine (from step 6a, 59 mg, 0.3 mmol) was dissolved in Et$_2$O (8 mL), and Et$_2$O saturated with HCl (g) was added. The solvent was removed, and the precipitate was recrystallized from MeOH/Et$_2$O to afford a white solid (54 mg, 77%). mp 185°–186° C. MS (CI/NH$_3$) m/e: 207 (M+H)$^+$. $^1$H NMR D$_2$O, 300 MHz) a 2.06–2.21 (m, 2H), 2.27–2.41 (m, 4H), 2.65–2.77 (m, 2H), 3.32–3.40 (m, 2H), 3.85–3.95 (m, 2H), 7.47 (ddd, J=7.7, 4.8, 1.8 Hz, 1H), 8.14 (ddd, J=10.7, 7.7, 1.8 Hz, 1H), 8.27 (ddd, J=4.8, 1.8, 1.1 Hz, 1H). Anal. Calcd for C$_{12}$H$_{16}$ClFN$_2$: C, 59.38; H, 6.64; N, 11.54. Found: C, 59.14; H, 6.53; N, 11.34.

Example 7

7a-(2-chloro-3-pyridinyl)-hexahydro-1H-pyrrolizine hydrochloride 7a. 7a-(2-chloro-3-pyridinyl)-hexahydro-1H-pyrrolizine A solution of 2.5M nBuLi (680 μL, 1.7 mmol) in hexanes was added to diisopropylamine (0.220 mL, 1.7 mmol) in THF (4.5 mL) at ambient temperature. After 10 minutes of stirring the reaction mixture was cooled to −78° C., 2-chloropyridine was added neat, and sting continued for 4 hours at −78° C. 1,2,3,5,6,7-hexahydro-pyrrolizinium perchlorate (500 mg, 2.4 mmol) was added, and the reaction mixture was allowed to stir for 2 hours at −78° C. then warm to ambient temperature. A solution of 2N HCl was added, and the mixture was poured over EtOAc. The phases were separated, and the aqueous phase was basified with 15% NaOH and extracted with CH$_2$Cl$_2$ (2×). The CH$_2$Cl$_2$ fractions were combined, dried (MgSO$_4$) and concentrated, and the residue was chromatographed (silica gel; CHCl$_3$/MeOH, 100:0 to 99.5:0.5) to afford yellow oil (18 mg, 5%). $R_f$=0.30 (CHCl$_3$/MeOH, 99:1). MS (CI/NH$_3$) m/e: 223 (M+H)$^+$. $^1$H NMR (CDCl$_3$, 300 MHz) δ1.50–1.61 (m, 2H), 1.78–1.89 (m, 2H), 2.10–2.29 (m, 4H), 2.69–2.75 (m, 2H), 3.04–3.11 (m, 2H), 7.17 (dd, J=7.7, 4.8 Hz, 1H), 8.21 (dd, J=4.8, 1.8 Hz, 1H), 8.36 (dd, J=7.7, 1.8 Hz, 1H).

7b. 7a-(2-chloro-3-pyridinyl)-hexahydro-1H-pyrrolizine hydrochloride salt 7a-(2-Chloro-3-pyridinyl)-hexahydro-1H-pyrrolizine (21 mg, 0.1 mmol) was dissolved in Et$_2$O (6 mL), and Et$_2$O saturated with HCl (g) was added. The solvent was removed, and the precipitate was triturated (3×) with Et$_2$O to afford a yellow solid (26 mg, quant). mp 186°–188° C. MS (CI/NH$_3$) m/e: 223 (M+H)$^+$. $^1$H NMR D$_2$O, 300 MHz) δ2.03–2.18 (m, 2H), 2.29–2.41 (m, 2H), 2.54–2.64 (m, 2H), 2.75–2.84 (m,2H), 3.41–2.51 (m, 2H), 2.93–4.02 (m, 2H), 7.57 (dd, J=8.1, 4.7 Hz, 1H), 8.01 (dd, J=8.1, 1.7 Hz, 1H), 8.42 (dd, J=4.7, 1.7 Hz, 1H). Anal. Calcd for Cl$_2$H$_{16}$Cl$_2$N$_2$: C, 55.61; H, 6.22; N, 10.81. Found: C, 55.21; H, 6.25; N, 10.45

Example 8

7a-(5,6-dichloro-3-pyridinyl)-hexahydro-1H-pyrrolizine hydrochloride 8a. 2,3-Dichloro-5-iodopyridine 5-Amino-2,3-dichloropyridine (15.0 g, 92.0 mmol, prepared according to V. Koch and S. Schnatterer, *Synthesis*, 1990, 499–501) was dissolved in DME (30 mL) and subjected to diazotization conditions according to the procedure of M. P. Doyle and W. J. Bryker (*Journal Of Organic Chemistry*, 1979, 44, 1572). The dissolved pyridine analog was added to a solution of BF$_3$ etherate complex (17 mL, 138 mmol) at −15° C. t-Butyl nitrite in DME (92 mL) was then added at a rate such that the temperature never rose above −5° C. After complete addition, the reaction mixture was allowed to warm to 5° C. and stir an additional 45 minutes. Pentane was added and the resultant slurry filtered. The filter cake was washed with cold Et$_2$O, and the solid was air dried to afford a light orange solid (22.3 g). A sample of the crude diazonium tetrafluoroborate salt (5.1 g, 19.5 mmol) and KI (3.5 g, 21.4 mmol) were combined in CH$_3$CN (130 mL) and allowed to stir at ambient temperature for 18 hours. A 10% solution of Na$_2$S$_2$O$_3$ was carefully added, the biphasic mixture was poured over Et$_2$O, and the phases were separated. The organic phase was dried (MgSO$_4$) and concentrated, and the residue was chromatographed (silica gel; hexanes/CH$_2$Cl$_2$, 10:1) to afford a white solid (4.0 g, 75%). mp 55°–57° C. $R_f$=0.43 (hexanes/CH$_2$Cl$_2$, 2:1). $^1$H NMR (CDCl$_3$, 300 MHz) δ8.09 (d, J=1.8 Hz, 1H), 8.5 (d, J=1.8 Hz, 1H).

8b. 7a-(5,6-dichloro-3-pyridinyl)-hexahydro-1H-pyrrolizine

A solution of 1.7M tBuLi (4.7 mL, 8.0 mmol) in pentane was added to 2,3-dichloro-5-iodopyridine (from step 8a, 1.0 g, 3.65 mmol) in Et$_2$O (15 mL) precooled to −100° C. After stirring for 2 minutes, 1,2,3,5,6,7-hexahydropyrrolizinium perchlorate (1.5 g, 7.3 mmol) was added, and the reaction mixture was allowed to stir for 20 minutes at −100° C. then gradually warm to −20° C. A solution of 2N HCl was added, and the cold bath was removed. After warming to ambient temperature, the reaction mixture was poured over EtOAc and the phases were separated. The aqueous phase was basified with 15% NaOH solution and extracted with $CH_2Cl_2$ (2×). The $CH_2Cl_2$ phases were combined, dried ($MgSO_4$), concentrated and the residue was chromatographed (silica gel; $CHCl_3$/MeOH, 99.5:0.5) to afford a light yellow oil (510 mg, 54%). MS (CI/$NH_3$) m/e: 257 (M+H)$^+$. $^1$H NMR (CDCl$_3$, 300 MHz) δ1.59–1.71 (m, 2H), 1.80–2.08 (m, 6H), 2.64–2.72 (m, 2H), 3.11–3.20 (m, 2H), 7.99 (d, J=2.2 Hz, 1H), 8.36 (d, J=2.2 Hz, 1H).

8c. 7a-(5,6-dichloro-3-pyridinyl)-hexahydro-1H-pyrrolizine hydrochloride salt 7a-(5,6-dichloro-3-pyridinyl)-hexahydro-1H-pyrrolizine (from step 8b, 128 mg, 0.50 mmol) was slurried in Et$_2$O (8 mL), and Et$_2$O saturated with HCl (g) added. The solvent was removed, and the solid was recrystallized from MeOH/Et$_2$O to afford a white solid (111 mg, 75%). mp 215°–217° C. MS (CI/NH$_3$) m/e: 257 (M+H)$^+$. $^1$H NMR D$_2$O, 300 MHz) δ2.12–2.50 (m, 6H), 2.54–2.65 (m, 2H), 3.35–3.43 (m, 2H), 3.79–3.88 (m, 2H), 8.21 (d, J=2.4 Hz, 1H), 8.47 (d, J=2.4 Hz, 1H). Anal. Calcd for $C_{12}H_{15}C_{13}N_2$: C, 49.09; H, 5.15; N, 9.54. Found: C, 49.01; H, 5.15; N, 9.44.

Example 9

7a-(5-pyrimidinyl)-hexahydro-1H-pyrrolizine hydrochloride 9a. 7a-(5-pyrimidinyl)-hexahydro-1H-pyrrolizine A solution of 1.7M tBuLi (1.6 mL, 2.6 mmol) in pentane was added to 5-bromopyrimidine (190 mg, 1.2 mmol) in Et$_2$O:THF (1:1, 12 mL) at −100° C. After stirring for 10 minutes, 1,2,3,5,6,7-hexahydropyrrolizinium perchlorate (500 mg, 2.4 mmol) was added to the reaction slurry, and stirring was continued for 30 minutes. The reaction mixture was then allowed to warm to 0° C. and stir for 1 hour. A solution of 2N HCl was added, and the reaction mixture was poured over Et$_2$O and the phases separated. The aqueous phase was basified with 15% NaOH solution and extracted with CH$_2$Cl$_2$ (2×). The CH$_2$Cl$_2$ phases were combined, dried (MgSO$_4$), concentrated, and the residue was chromatographed (silica gel; CHCl$_3$/MeOH, 98:2) to afford a clear oil (40 mg, 18%). MS (CI/NH$_3$) m/e: 190 (M+H)$^+$. $^1$H NMR (CDCl$_3$, 300 MHz) δ1.60–1.73 (m, 2H), 1.82–2.11 (m, 6H), 2.66–2.75 (m, 2H), 3.15–3.21 (m, 2H), 8.85 (s, 2H), 9.05 (s,1H).

9b. 5-(7a-Hexahydro-1H-pyrrolizinyl)pyrimidine hydrochloride salt 7a-(5-Pyrimidinyl)-hexahydro-1H-pyrrolizine (from step 9a, 33 mg, 0.2 mmol) was slurried in Et$_2$O (7 mL), and HCl saturated with HCl (g) was added. The solvent was removed to afford a hygroscopic white solid (23 mg, 60%). MS (CI/NH$_3$) m/e: 190 (M+H)$^+$. $^1$H NMR D$_2$O, 300 MHz) δ2.13–2.70 (m, 8H), 3.38–3.46 (m, 2H), 3.81–3.90 (m, 2H), 8.99 (s, 2H), 9.17 (s, 1H). Anal. Calcd for $C_{11}H_{16}ClN_3$·0.5 HCl: C, 54.16; H, 6.82; N, 17.22. Found: C, 54.42; H, 7.26; N, 16.95.

Example 10

7a-(2,6-difluoro-3-pyridinyl)-hexahydro-1H-pyrrolizine hydrochloride 10a. 7a-(2,6-difluoro-3-pyridinyl)-hexahydro-1H-pyrrolizine A solution of 2.5M nBuLi (675 μL, 1.7 mmol) in hexanes was added to diisopropylamine (220 μL, 1.6 mmol) in THF (4.5 mL) at ambient temperature. After 10 minutes of stirring, the reaction mixture was cooled to −78° C., 2,6-difluoropyridine (145 μL, 1.6 mmol) was introduced, and stirring was continued for 1 hour at −78° C. 1,2,3,5,6,7-hexahydropyrrolizinium perchlorate (500 mg, 2.4 mmol) was then added, and the cold bath was removed. After warming to ambient temperature, a solution of 2N HCl was added and the phases were separated after pouting the reaction mixture over EtOAc. The aqueous phase was basified with 15% NaOH solution and extracted with CH$_2$Cl$_2$ (2×). The CH$_2$Cl$_2$ extracts were combined, dried (MgSO$_4$), concentrated and chromatographed (silica gel; CHCl$_3$/MeOH, 98:2) to afford a clear oil (180 mg, 50%). MS (CI/NH$_3$) m/e: 225 (M+H)$^+$. $^1$H NMR (CDCl$_3$, 300 MHz) δ1.5–1.63 (m, 2H), 1.78–1.89 (m, 2H), 1.92–2.10 (m, 4H), 2.63–2.70 (m, 2H), 3.08–3.12 (m, 2H), 6.72 (dd, J=8.1, 3.0 Hz, 1H), 8.33 (dd, J=18.0, 8.1 Hz, 1H).

10b. 7a-(2,6-difluoro-3-pyridinyl-hexahydro-1H-pyrrolizine hydrochloride salt

A solution of Et$_2$O saturated with HCl (g) was added to 7a-(2,6-difluoro-3-pyridinyl)-hexahydro-1H-pyrrolizine (from step 10a, 174 mg, 0.8 mmol) in Et$_2$O (10 mL). The slurry was filtered, and the filter cake was washed with Et$_2$O to afford a white solid (138 mg, 68%). mp 205°–206° C. MS (CI/NH$_3$) m/e: 225 (M+H)$^+$. $^1$H NMR D$_2$O, 300 MHz) δ2.08–2.21 (m, 2H), 2.26–2.40 (m, 4H), 2.64–2.73 (m, 2H), 3.31–3.40 (m, 2H), 3.82–3.90 (m, 2H), 7.14 (dd, J=8.5, 2.7 Hz, 1H), 8.22–8.30 (m, 1H). Anal. Calcd for $C_{12}H_{15}ClF_2N_2$: C, 54.92; H, 5.70; N, 10.52. Found: C, 55.28; H, 5.80; N, 10.74

Example 11

7a-(2,6-dichloro-3-pyridinyl)-hexahydro-1H-pyrrolizine hydrochloride salt 11a. 7a-(2,6-dichloro-3-pyridinyl)-hexahydro-1H-pyrrolizine A solution of 2.5M nBuLi (675 μL, 1.7 mmol) in hexanes was added to diisopropylamine (220 μL, 1.7 mmol) in THF (4.5 mL) at ambient temperature. After 10 minutes of stirring, the reaction mixture was cooled to −78° C., 2,6-dichloropyridine (237 μL, 1.60 mmol) was added neat, and stirring was continued for 1 hour at −78° C. 1,2,3,5,6,7-hexahydropyrrolizinium perchlorate (500 mg, 2.40 mmol) was added, and the reaction mixture was allowed to stir for 2 hours at −78° C. then warm to ambient temperature. A solution of 2N HCl was added, and the mixture was then poured over EtOAc. The phases were separated, and the aqueous phase was basified with 15% NaOH and extracted with CH$_2$Cl$_2$ (2×). The CH$_2$Cl$_2$ fractions were combined, dried (MgSO$_4$) and concentrated, and the residue was chromatographed (silica gel; CHCl$_3$/MeOH, 98:2) to afford a clear oil (70.6 mg, 17%). MS (CI/NH$_3$) m/e: 257/259 (M+H)$^+$. $^1$H NMR (CDCl$_3$, 300 MHz) δ1.47–1.61 (m, 2H), 1.77–1.90 (m, 2H), 2.10–2.25 (m, 4H), 2.67–2.75 (m, 2H), 3.03–3.11 (m, 2H), 7.19 (d, J=8.5 Hz, 1H), 8.37 (d, J=8.5 Hz, 1H).

11b. 7a-(2,6-dichloro-3-pyridinyl)-hexahydro-1H-pyrrolizine hydrochloride salt 7a-(2,6-dichloro-3-pyridinyl)-hexahydro-1H-pyrrolizine (from step 11a, 62 mg, 0.24 mmol) was dissolved in Et$_2$O, and Et$_2$O saturated with HCl (g) was added. The solvent was removed, and the precipitate was triturated with Et$_2$O to give a white solid (35.6 mg). mp 212°–214° C. 1H NMR D$_2$O, 300 MHz) δ2.02–2.18 (m, 2H), 2.28–2.41 (m, 2H), 2.52–2.64 (m, 2H), 2.72–2.83 (m, 2H), 3.41–3.50 (m, 2H), 3.92–4.02 (m, 2H), 7.60 (d, J=8.5 Hz, 1H), 8.00 (d, J=8.5 Hz, 1H); MS (ClfNH$_3$) m/z: 257/259 (M+H)$^+$. Anal. Calcd for $C_{12}H_{16}ClFN_2$: C, 49.26; H, 4.82; N, 9.57. Found: C, 49.14; H, 5.03; N, 9.47.

Example 12

7a-(6-fluoro-3-pyridinyl)-hexahydro-1H-pyrrolizine hydrochloride salt 12a. 2-Fluoro-5-nitropyridine 2-Chloro-5-nitropyridine (100 g, 0.656 mol, Aldrich), KF (84.1 g, 1.448 mol), Ph$_4$PBr (95.3 g, 0.227 mol) and acetonitrile (1.5 L) were combined and heated at reflux until no starting material remained. The volume was reduced to 750 mL, and the mixture was diluted with 2 L of ether, filtered and concentrated. The residue was triturated with hot hexane (5×1 L). The hexane extracts were combined and concentrated to afford 48 g (54%). $^1$H NMR (CDCl$_3$, 300 MHz) δ7.15 (dd, J=3, 6 Hz, 1H), 8.64 (m, 1H), 9.15 (d, J=1.6 Hz, 1H).

12b. 5-Amino-2-fluoropyridine

2-Fluoro-5-nitropyridine (52.35 g, 368 mmol, from step 12a) was combined with 5% Pd/C (100 mg) in EtOH (100 mL), and the mixture was stirred under a H$_2$ atmosphere for 4 days. The mixture was filtered and concentrated, and the residue was chromatographed (silica gel;/EtOAc/hexane, 1:9 to 1:1) to afford 30.9 g (75%)of the title compound: $^1$H NMR (DMSOd-$_6$ 300 MHz) δ6.74 (dd, J=3, 6 Hz, 1H), 7.11 (m, 1H), 7.26 (t, J=1 Hz, 1H); MS (CI/NH$_3$) m/z: 113 (M+H)$^+$, 130 (M+NH$_4$)$^+$.

12c. 2-Fluoro-5-iodopyridine

5-Amino-2-fluoropyridine (990 mg, 8.83 mmol, from step 12b) in DME (5 mL) was added dropwise to a solution of boron trifluoride diethyl etherate (1.6 mL, 13.2 mmol) at −10° C. After stirring for 15 min, t-butyl nitrite in DME (15 mL) was carefully added to the reaction mixture while maintaining the temperature below −5° C. After complete addition the temperature was allowed to gradually warm to 5° C. over 1 hour. The solution was recooled to −10° C., the residue was triturated with pentane (2×) and Et$_2$O, then all solvents were removed in vacuo. The crude diazonium tetrafluoroborate salt was dissolved in acetonitrile (50 mL), KI was added (1.6 g, 9.7 mmol) and the mixture was stirred for 24 hours. A solution of 10% sodium thiosulfate was carefully added, the mixture was poured over Et$_2$O and the phases separated. The organic phase was dried (MgSO$_4$) and concentrated, and the residue was chromatographed (silica gel; EtOAc/hexane, 1:20) to afford a white solid (1.2 g, 59%): $^1$H NMR (CDCl$_3$, 300 MHz) δ6.79 (dd, J=8.4, 2.6 Hz, 1H), 8.04 (ddd, J=8.4, 7.4 2.6 Hz, 1H), 8.43 (dd, 2.6, 0.7 Hz, 1H).

12d. 7a-(6-fluoro-3-pyridinyl)-hexahydro-1H-pyrrolizine

2-Fluoro-5-iodopyridine (200 μL, 0.90 mmol) was dissolved in Et$_2$O and cooled to −78° C. A solution of 2.5M t-BuLi (1.2 mL, 1.98 mmol) in pentane was added, and the reaction was stirred for 2 minutes. 1,2,3,5,6,7-hexahydropyrrolizinium perchlorate (375 mg, 1.80 mmol) was added, and the reaction mixture was allowed to stir for 10 minutes at −78° C. then allowed to warm to −20° C. The cold bath was removed, 2N HCl was added, and the mixture was extracted with Et$_2$O. The phases were separated, and the aqueous phase was basified with 15% NaOH and extracted with CH$_2$Cl$_2$ (2×). The CH$_2$Cl$_2$ fractions were combined, dried (MgSO$_4$) and concentrated, and the residue was chromatographed (silica gel; CHCl$_3$/MeOH, 98:2) to afford a clear oil (75 mg, 40%). $^1$H NMR (CDCl$_3$, 300 MHz) δ1.58–1.73 (m, 2H), 1.79–2.05 (m, 6H), 2.64–2.73 (m, 2H), 3.12–3.19 (m, 2H), 6.82 (dd, J=8.4, 2.7 Hz, 1H), 7.90 (m, 1H), 8.30 (dd, J=1.4, 0.7 Hz, 1H); MS (CI/NH$_3$) m/z: 207 (M+H)$^+$.

12e. 7a-(5-fluoro-3-pyridinyl)-hexahydro-1H-pyrrolizine hydrochloride salt 7a-(5-fluoro-3-pyridinyl)-hexahydro-1H-pyrrolizine (62 mg, 0.24 mmol, from step 12d) was dissolved in Et$_2$O, and Et$_2$O saturated with HCl (g) was added. The solvent was removed, and the precipitate was triturated with to give a white solid (57.1 mg, 69%). mp 168°–169° C. $^1$H NMR D$_2$O, 300 MHz) 67 2.13–2.50 (m, 6H), 2.58–2.67 (m, 2H), 3.34–3.42 (m, 2H), 3.78–3.87 (m, 2H), 7.24 (dd, J=8.8, 2.4, Hz, 1H), 8.13 (ddd, J=8.8, 7.2, 2.7 Hz, 1H), 8.36 (dd, J=2.7, 1.4 Hz, 1H); MS (CI/NH$_3$) m/z: 207 (M+H)$^+$. Anal. Calcd for Cl$_{12}$H$_{16}$ClFN$_2$: C, 59.38; H, 6.64; N, 11.54. Found: C, 59.51; H, 6.52; N, 11.30.

Example 13

7a-(3-ethyl-5-isoxazolyl)-hexahydro-1H-pyrrolizine hydrochloride salt 13a. 7a-Ethynyl-hexahydro-1H-pyrrolizine 1,2,3,5,6,7-Hexahydropyrrolizinylium perchlorate (1.0 g, 4.8 mmol) was added to a solution of 0.5M ethynylmagnesium bromide (29 mL, 14.3 mmol) in THF at room temperature. The reaction mixture was allowed to stir for 45 minutes, and 15% NaOH solution was added. The slurry was diluted with brine:water (1:1) and extracted with CH$_2$Cl$_2$ (3×). The organic phases were combined, dried (MgSO$_4$), concentrated and chromatographed (silica gel; CHCl$_3$/MeOH, 90:10) to afford an amber oil (463 mg, 71%): $^1$H NMR (CDCl$_3$, 300 MHz) δ1.75–2.06 (m, 6H), 2.14–2.23 (m, 2H), 2.33 (s, 1H), 2.53–2.62 (m, 2H), 3.22–3.28 (m, 2H); MS (CI/NH$_3$) m/z: 136 (M+H)$^+$.

13b. 7a-(3-ethyl-5-isoxazolyl)-hexahydro-1H-pyrrolizine

Nitropropane (0.475 mL, 5.29 mmol) and phenylisocyanate (1.0 mL, 9.5 mmol) were dissolved in benzene (10 mL) and added to a flask containing 7a-ethynyl-hexahydro-1H-pyrrolizine (358 mg, 2.65 mmol, from step 13a). The solution was stirred at ambient temperature for 1 hour and at reflux for 5 hours. The mixture was cooled, filtered, concentrated and diluted with EtOAc. The solution was extracted with 6N HCl. The aqueous phase was made basic with 15% NaOH and extracted with methylene chloride. The organic extracts were combined, dried (MgSO$_4$) and concentrated. The residue was residue was chromatographed (silica gel; CHCl$_3$/MeOH, 98:2) to afford an amber oil (274 mg, 50%). $^1$H NMR (CDCl$_3$, 300 MHz) δ1.25 (t, J=7.5 Hz, 3H), 1.75–1.92 (m, 6H), 2.15–2.25 (m, 2H), 2.60–2.69 (m, 4H), 3.13–3.20 (m, 2H), 5.98 (s, 1H); MS (CI/NH$_3$) m/z: 207 (M+H)$^+$.

13c. 7a-(3-ethyl-5-isoxazolyl)-hexahydro-1H-pyrrolizine hydrochloride salt 7a-(3-ethyl-5-isoxazolyl)-hexahydro-1H-pyrrolizine (265 mg, 1.30 mmol, from step 13b) was dissolved in Et$_2$O, and Et$_2$O saturated with HCl (g) was added. The solvent was removed, and the precipitate was recrystallized from methanol/ethanol to afford the title compound as a white solid: mp 139°–140° C.; $^1$H NMR D$_2$O, 300 MHz) δ1.23 (t, J=7.5 Hz, 3H), 2.17–2.40 (m, 6H), 2.58–2.75 (m, 4H), 3.29–3.38 (m, 2H), 3.69–3.77 (m, 2H), 6.64 (s, 1H); MS (CI/NH$_3$) m/z: 207 (M+H)$^+$; Anal. Calcd for C$_{12}$H$_{18}$N$_2$O.HCl: C, 59.38; H, 7.89; N, 11.54. Found: C, 59.44; H, 7.94; N, 11.48.

Example 14

7a-(3-propyl-5-isoxazolyl)-hexahydro-1H-pyrrolizine hydrochloride salt 14a. 7a-(3-propyl-5-isoxazolyl)-hexahydro-1H-pyrrolizine Nitrobutane (0.705 mL, 6.66 mmol) and phenylisocyanate (1.50 mL, 13.3 mmol) were dissolved in benzene (13.5 mL) and added to a flask containing 7a-ethynyl-hexahydro-1H-pyrrolizine (450 mg, 3.33 mmol, from step 13a). The solution was stirred at ambient temperature for 1 hour and at reflux for 5 hours. The mixture was cooled, filtered, concentrated and diluted with EtOAc. The solution was extracted with 6N HCl. The aqueous phase was made basic with 15% NaOH and extracted with methylene chloride. The organic extracts were combined, dried (MgSO$_4$) and concentrated. The residue was residue was chromatographed (silica gel; CHCl$_3$/MeOH, 98:2) to afford an amber oil (392 mg, 53%). $^1$H NMR (CDCl$_3$, 300 MHz) δ0.97 (t, J=7.5 Hz, 3H), 1.61–1.92 (m, 8H), 2.15–2.26 (m, 2H), 2.55–2.69 (m, 4H), 3.13–3.20 (m, 2H), 5.96 (s, 1H); MS (CI/NH$_3$) m/z: 221 (M+H)$^+$.

14b. 7a-(3-propyl-5-isoxazolyl)-hexahydro-1H-pyrrolizine hydrochloride salt 7a-(3-propyl-5-isoxazolyl)-hexahydro-1H-pyrrolizine (265 mg, 1.30 mmol, from step 14a) was dissolved in Et$_2$O, and Et$_2$O saturated with HCl (g) was added. The solvent was removed, and the precipitate was triturated with Et$_2$O and dried to afford the title compound as a free flowing white powder. mp 97°–98° C. MS (NH$_3$/CI): m/z 207 (M+H$^+$); $^1$H NMR (D$_2$O, 300 MHz) δ0.92 (t, J=7.5 Hz, 3H), 1.63–1.75 (m, 2H), 2.20–2.40 (m, 6H), 2.59–2.71 (m, 4H), 3.30–3.38 (m, 2H), 3.70–3.78,(m, 2H), 6.65 (s, 1H); MS (CI/NH$_3$) m/z: 221 (M+H)$^+$.Anal. Calcd for C$_{13}$H$_{20}$N$_2$O.HCl: C, 59.38; H, 7.89; N, 11.54. Found: C, 59.44; H, 7.94; N, 11.48.

Example 15

7a-(3-benzyl-5-isoxazolyl)-hexahydro-1H-pyrrolizine hydrochloride salt 15a. 2-phenylnitroethene Benzaldehyde (10.0 g, 94.2 mmol) and nitromethane (5.1 mL, 94.2 mmol) were dissolved in MeOH, the solution was cooled to –18° C., and NaOH (3.9 g, 98.9 mmol) in aqueous solution (80 mL) was added while maintaining the temperature below –10° C. The mixture was stirred at 0° C. for 2 hours, then stored at 5° C. overnight. The solution was then poured into stirring acid (200 mL conc. HCl/300 mL H$_2$O). The precipitate was collected, washed, and recrystallized from EtOH to afford the title compound as light orange needles (5.15 g, 37%).

15b. 2-phenylnitroethane

2-Phenylnitroethene (5.12 g, 34.3 mmol, from step 15a) was dissolved in CHCl$_3$/i-PrOH (410:85 mL) and SiO$_2$ (51.4 g) was added. NaBH$_4$ (5.2 g, 137 mmol) was added in portions, and the mixture was stirred for 90 minutes at room temperature. HCl (0.5N, 100, mL) was added, and the mixture was stirred for 30 minutes. The layers were separated, and the aqueous phase was extracted with methylene chloride. The organic layers were combine, dried (MgSO$_4$) and concentrated. The residue was chromatographed on silica gel (eluting with ether:hexanes 1:30) to give the title compound as an oil (3.89 g, 75%).

15c. 7a-(3-benzyl-5-isoxazolyl)-hexahydro-1H-pyrrolizine

2-Phenylnitroethane (895 mg, 5.92 mmol, from step 15b) and phenylisocyanate (1.3 mL, 11.8 mmol) were dissolved in benzene (12 mL) and added to a flask containing 7a-ethynyl-hexahydro-1H-pyrrolizine (400 mg, 2.96 mmol, from step 13a). The solution was stirred at reflux for 5 hours, cooled and stirred for 48 hours at room temperature. The mixture was filtered and extracted with 6N HCl. The aqueous phase was made basic with 15% NaOH and extracted with methylene chloride. The organic extracts were combined, dried (MgSO$_4$) and concentrated. The residue was chromatographed (silica gel; CHCl$_3$/MeOH, 99:1) to afford an amber oil (415 mg, 52%). $^1$H NMR (CDCl$_3$, 300 MHz) δ1.71–1.92 (m, 6H), 2.11–2.23 (m, 2H), 2.58–2.66 (m, 2H), 3.08–3.15 (m, 2H), 3.95 (s, 2H), 5.87 (s, 1H), 7.20–7.34 (m, 5H); MS (CI/NH$_3$) m/z: 269 (M+H)$^+$.

15d. 7a-(3-benzyl-5-isoxazolyl)-hexahydro-1H-pyrrolizine hydrochloride salt 7a-(3-Benzyl-5-isoxazolyl)-hexahydro-1H-pyrrolizine (407 mg, 1.52 mmol, from step 15c) was dissolved in Et$_2$O, and Et$_2$O saturated with HCl (g) was added. The solvent was removed, and the precipitate was recrystallized from MeOH and dried to afford the title compound as white needles: mp 126°–127° C.; $^1$H NMR D$_2$O, 300 MHz) δ2.17–2.36 (m, 6H), 2.53–2.62 (m, 2H), 3.28–3.36 (m, 2H), 3.67–3.75 (m, 2H), 4.08 (s, 2H), 6.57 (s, 1H), 7.34–7.45 (m, 5H); MS (CI/NH$_3$) m/z: 269 (M+H)+; Anal. Calcd for C$_{17}$H$_{20}$N$_2$O.HCl: C, 66.99; H, 6.94; N, 9.19. Found: C, 66.99; H, 6.87; N, 9.09.

Example 16

7a-(3-hydroxy-5-pyridinyl)-hexahydro-1H-pyrrolizine hydrochloride salt 16a. 3-Benzyloxy-5-bromopyridine Sodium hydride (60% in mineral oil, 40.9 g, 1.0 mol) in DMF (800 mL) was cooled to 0° C., and benzyl alcohol (105 mL, 1.0 mol) was slowly added. After stirring for 1 hour at ambient temperature, 3,5-dibromopyridine (200.4 g, 846 mmol) was added and the mixture allowed to stir for 16 hours. Saturated NH$_4$Cl solution (500 mL) was added followed by water (400 mL), and the mixture was extracted with Et$_2$O (5×300 mL). The combined Et$_2$O extracts were washed with 50% brine (6×300 mL), dried (MgSO$_4$), concentrated and the residue recrystallized from Et$_2$O to afford a white solid (161 g, 72%): $^1$H NMR (CDCl$_3$, 300 MHz) δ5.10 (s, 2H), 7.50–7.35 (m, 6H), 8.37–8.27 (m, 2H); MS (CI/NH$_3$) m/z: 264/266 (M+H)$^+$.

16b. 7a-(3-benzyloxy-5-pyridinyl)-hexahydro-1H-pyrrolizine

3-Benzyloxy-5-bromopyridine (1.18 g, 4.47 mmol) was dissolved in Et$_2$O and cooled to –78° C. A solution of 2.5M t-BuLi (5.8 mL, 9.83 mmol) in pentane was added, and the reaction was stirred for 10 minutes. 1,2,3,5,6,7-hexahydropyrrolizinium perchlorate (1.4 g, 6.70 mmol) was added, and the reaction mixture was allowed to stir for 3 hours at –78° C. then allowed to warm to –20° C. and stir for 2 hours. The cold bath was removed, 2N HCl was added, and the mixture was extracted with Et$_2$O. The phases were separated, and the aqueous phase was basified with 15% NaOH and extracted with CH$_2$Cl$_2$ (2×). The CH$_2$Cl$_2$ fractions were combined, dried (MgSO$_4$) and concentrated, and the residue was chromatographed (silica gel; CHCl$_3$/MeOH, 98:2) to afford a clear oil (286 mg, 22%): mp 45°–49° C. $^1$H NMR (CDCl$_3$, 300 MHz) δ1.58–1.69 (m, 2H), 1.78–1.83 (m, 2H), 1.89–2.03 (m, 4H), 2.63–2.72 (m, 2H), 3.05–3.18 (m, 2H), 5.12 (s, 2H), 7.31–7.54 (m, 6H), 8.17 (d, J=3.0 Hz, 1H), 8.29 (d, J=1.7 Hz, 1H); MS (CI/NH$_3$) m/z: 295 (M+H)$^+$.

16c. 7a-(3-hydroxy-5-pyridinyl)-hexahydro-1H-pyrrolizine 7a-(3-Benzyloxy-5-pyridinyl)-hexahydro-1H-pyrrolizine (260 mg, 0.88 mmol, from step 16b) was dissolved in methanol (9 mL), 10% Pt/C (35 mg) was added, and the mixture stirred under 1 arm of H$_2$ for 16 hours. The catalyst was removed, the filtrate was concentrated, and the residue was chromatographed (silica gel; CHCl$_3$/MeOH/0.5 % NH$_4$OH, 90:10:0 to 90:10:0.5) to afford the title compound as a white solid (114 mg, 63%). $^1$H NMR D$_2$O, 300 MHz) δ2.07–2.40 (m, 6H), 2.49–2.58 (m, 2H), 3.26–3.34 (m, 2H), 3.71–3.80 (m, 2H), 7.00 (dd, J=2.4, 2.0 Hz, 1H), 7.80 (d, J=2.0 Hz, 1H), 7.85 (d, J=2.4 Hz, 1H); MS (CI/NH$_3$) m/z: 205 (M+H)$^+$.

16d. 7a-(3-hydroxy-5-pyridinyl)-hexahydro-1H-pyrrolizine hydrochloride salt 7a-(3-Hydroxy-5-pyridinyl)-hexahydro-1H-pyrrolizine (150 mg, 0.56 mmol, from step 16c) was dissolved in methylene chloride, and Et₂O saturated with HCl (g) was added. The solvent was removed, and the solid was dried to afford the title compound as a white powder (114 mg, 91%): mp 175°–180° C. (dec.); $^1$H NMR D₂O, 300 MHz) δ2.11–2.63 (m, 8H), 3.35–3.44 (m, 2H), 3.80–3.89 (m, 2H), 7.66 (dd, J=2.4, 2.0 Hz, 1H), 8.23 (d, J=2.4 Hz, 1H), 8.29 (d, J=2.0 Hz, 1H); MS (CI/NH₃) m/z: 205 (M+H)⁺. Anal. Calcd for C12H16N2O.HCl: C, 53.40; H, 6.65; N, 10.38. Found: C, 53.55; H, 6.62; N, 10.24.

Example 17

7a-(5-bromo-3-pyridinyl)-hexahydro-1H-pyrrolizine hydrochloride salt 17a. 7a-(5-bromo-3-pyridinyl)-hexahydro-1H-pyrrolizine 3,5-dibromopyridine (500 mg, 2.11 mmol, Aldrich) was dissolved in Et₂O and cooled to −95° C. A solution of 2.5M t-BuLi (1.7M in pentane, 2.7 mL, 4.64 mmol) in pentane was added dropwise. 1,2,3,5,6,7-hexahydropyrrolizinium perchlorate (663 mg, 3.2 mmol) was added, and the reaction mixture was allowed to stir and warm to −10° C. and stir for 2 hours. The cold bath was removed, 2N HCl was added, and the phases were separated. The aqueous phase was basified with 15% NaOH and extracted with CH₂Cl₂ (2×). The CH₂Cl₂ fractions were combined, dried (MgSO₄) and concentrated, and the residue was chromatographed (silica gel; CHCl₃/MeOH, 98:2) to afford a clear oil (160 mg, 28%): $^1$H NMR (CDCl₃, 300 MHz) 67 1.57–1.71 (m, 2H), 1.79–2.04 (m, 6H), 2.62–2.73 (m, 2H), 3.11–3.20 (m, 2H), 8.04 (dd, J=2.0, 2.0 Hz, 1H), 8.46 (d, J=2.0 Hz, 1H), 8.58 (d, J=2.0 Hz, 1H); MS (CI/NH₃) m/z: 267/269 (M+H)⁺.

17b. 7a-(5-bromo-3-pyridinyl)-hexahydro-1H-pyrrolizine hydrochloride salt 7a-(5-bromo-3-pyridinyl)-hexahydro-1H-pyrrolizine (107 mg, 0.52 mmol, from step 16c) was dissolved in methylene chloride, and Et₂O saturated with HCl (g) was added. The solvent was removed, and the solid was crystallized from MeOH/Et₂O and dried to afford the title compound as an off-white powder (118 mg). mp 192°–194° C. $^1$H NMR D₂O, 300 MHz) δ2.13–2.51 (m, 6H), 2.57–2.66 (m, 2H), 3.36–3.44 (m, 2H), 3.81–3.89(m, 2H), 8.22 (s, 1H), 8.65 (s, 1H), 8.72 (s, 1H); MS (CI/NH₃) m/z: 267/269 (M+H)⁺. Anal. Calcd for C₁₂H₁₅BrN₂.HCl: C, 47.47; H, 5.31; N, 9.23. Found: C, 47.40; H, 5.22; N, 8.98.

Example 18

7a-(6-fluoro-5-methyl-3-pyridinyl)hexahydro-1H-pyrrolizine hydrochloride salt 18a. 2-fluoro-3-methyl-5-nitropyridine 2-Chloro-3-methyl-5-nitropyridine (15 g, 86.9 mmol; from Maybridge Chemical Co.), KF (12 g, 258 mmol) and tetraphenylphosphonium bromide (20 g, 47.7 mmol; Aldrich) were combined in 200 mL of acetonitrile and heated at reflux for 4 days. The mixture was diluted with Et₂O (500 mL) and filtered, and the filtrate was concentrated. The residue was triturated with hot hexane (4×200 mL), and the hexane solutions were combined and concentrated to afford the title compound as a solid (8.4 g, 60%): $^1$H NMR (DMSO-d₆, 300 MHz) δ2.42 (s, 3H), 8.43 (m, 1H), 8.95 (dd, J=1.6 Hz, 1H); MS (CI/NH₃) m/z: 157 (M+H)⁺.

18b. 5-amino-2-fluoro-3-methylpyridine

2-Fluoro-3-methyl-5-nitropyridine (8.2 g, mmol) combined with 5% Pd/C (100 mg) in EtOH (100 mL) under a H₂ atmosphere for 16 hours. The mixture was filtered and concentrated, and the crude product was chromatographed (silica gel; CHCl₃/MeOH 99:1 to 96:4) to afford a solid (5.2 g, 78% ): $^1$H NMR (DMSO-d₆, 300 MHz) δ2.10 (s, 3H), 5.11 (brs, 2H), 6.95 (dd, J=8.14 Hz, 1H), 7.26 (t, J=2.72 Hz, 1H); MS (CI/NH₃) m/z: 127 (M+H)⁺, 144 (M+NH₄)⁺.

18c. 2-fluoro-5-iodo-3-methylpyridine

5-Amino-2-fluoro-3-methylpyridine (397 mg, 3.1 mmol) in DME (1.7 mL) was added dropwise to a solution of boron trifluoride diethyl etherate (5.8 μL, 4.6 mmol) in DME (6 mL) at −17° C. After stirring for 15 min, t-butyl nitrite (442 μL, 3.7 mmol) neat was carefully added to the reaction mixture while maintaining the temperature below −5° C. After complete addition the temperature was allowed to gradually warm to 5° C. over 1 hr. After recooling to −17° C., pentane was added and then decanted. The light orange solid was triturated with pentane (2×) and Et₂O (2×) and then solvent was removed via positive N₂ pressure to afford a light orange solid. The crude diazonium tetrafluoroborate salt was dissolved in acetonitrile (6 mL) and KI (570 mg, 3.4 mmol) was added at −10° C. The reaction was allowed to gradually warm to ambient temperature and stir overnight. A solution of 10% sodium thiosulfate was carefully added to the reaction mixture which was then poured over Et₂O and the phases separated. The organic phase was dried (MgSO₄), concentrated and the residue chromatographed (silica gel; EtOAc/hexane, 1:50) to afford a white solid (500 mg, 68%): $^1$H NMR (DMSOd-₆, 300 MHz) 67 2.21 (s, 3H),), 8.21 (m, 1H), 8.27 (m, 1H).

18d. 7a-(6-fluoro-5-methyl-3-pyridinyl)-hexahydro-1H-pyrrolizine

2-Fluoro-5-iodo-3-methylpyridine (200 mg, 0.84 mmol) was dissolved in Et₂O and cooled to −95° C. A solution of 2.5M t-BuLi (1.7M in pentane, 1.1 mL, 1.80 mmol) in pentane was added dropwise. 1,2,3,5,6,7-hexahydropyrrolizinium perchlorate (265 mg, 1.26 mmol) was added, and the reaction mixture was allowed to warm to −10° C. with stirring for 2 hours. The cold bath was removed, 2N HCl was added, and the phases were separated. The aqueous phase was basified with 15% NaOH and extracted with CH₂Cl₂ (2×). The CH₂Cl₂ fractions were combined, dried (MgSO₄) and concentrated, and the residue was chromatographed (silica gel; CHCl₃/MeOH, 99:1) to afford the title compound as an oil (123 mg, 67%) $^1$H NMR (CDCl₃, 300 MHz) δ1.55–1.71 (m, 2H), 1.78–2.04 (m, 6H), 2.26 (s, 3H), 2.64–2.72 (m, 2H), 3.11–3.18 (m, 2H), 7.70 (m, 1H), 8.09 (m, 1H); MS (CI/NH₃) m/z: 221 (M+H)⁺.

18e. 7a-(6-fluoro-5-methyl-3-pyridinyl)-hexahydro-1H-pyrrolizine hydrochloride salt 7a-(6-Fluoro-5-methyl-3-pyridinyl)-hexahydro-1H-pyrrolizine (115 mg, 0.52 mmol, from step 18d) was dissolved in Et₂O, and Et₂O saturated with HCl (g) was added. The solvent was removed, and the solid was crystallized from MeOH/Et₂O and dried to afford the title compound (white needles, 92 mg, 69%): mp 170–171° C.; $^1$H NMR (D₂O, 300 MHz) δ2.12–2.47 (m, 9H), 2.56–2.66 (m, 2H), 3.32–3.41 (m, 2H), 3.77–3.86 (m, 2H), 7.94 (m, 1H), 8.14 (m, 1H); MS (CI/NH₃) m/z: 221 (M+H)⁺; MS (CI/NH₃): m/z 221 (M+H⁺). Anal. Calcd for C₁₃H₁₇FN₂.HCl: C, 60.82; H, 7.07; N, 10.91. Found: C, 60.83; H, 6.80; N, 10.63.

Example 19

7a-(6-chloro-5-methyl-3-pyridinyl)-hexahydro-1H-pyrrolizine hydrochloride salt 19a. 5-Amino-2-chloro-3-methylpyridine 2-Chloro-3-methyl-5-nitropyridine (15 g, 86.9 mmol; from Maybridge Chemical Co.) was dissolved in a solution of H₂O/AcOH (5:1, 60 mL). Iron powder was added to the reaction mixture while maintaining the temperature below 40° C., and the mixture was stirred for 5 hours. The mixture was filtered through celite and the aqueous filtrate was extracted with EtOAc (4×). The filter cake was washed with EtOAc, and the EtOAc solutions were combined, dried (MgSO$_4$), concentrated and chromatographed (silica gel; CHCl$_3$/MeOH, 98:2) to afford an orange solid (2.3 g, 89%): $^1$H NMR (CD$_3$OD, 300 MHz) δ2.25 (s, 3H), 7.01 (d, J=2.0 Hz, 1H), 7.58 (d, J=2.0 Hz, 1H); MS (CI/NH$_3$) m/z: 243/245 (M+H)$^+$.

19b. 2-Chloro-5-iodo-3-methylpyridine

5-Amino-2-chloro-3-methylpyridine (2.3 g, 16.3 mmol) in DME (9.0 mL) was added dropwise to a solution of boron trifluoride diethyl etherate (3.0 mL, 24.4 mmol) in DME (30.5 mL) at −17° C. After stirring for 15 min, t-butyl nitrite (442 µL, 3.7 mmol) in DME (30.5 mL) was carefully added to the reaction mixture while maintaining the temperature below −5° C. After complete addition the temperature was allowed to gradually warm to 5° C. over 1 hr. The mixture was recooled to −17° C., pentane was added and then decanted. The solid was triturated with pentane (3×) and Et$_2$O (3×) and then solvent was removed via positive N$_2$ pressure. The crude diazonium tetrafluoroborate salt was dissolved in acetonitrile (15 mL) and KI (3.0 g, 17.9 mmol) was added at −10° C. The reaction was allowed to gradually warm to ambient temperature and stir overnight. A solution of 10% sodium thiosulfate was carefully added to the reaction mixture which was then poured over Et$_2$O and the phases separated. The organic phase was dried (MgSO$_4$), concentrated and the residue chromatographed (silica gel; EtOAc/hexane, 1:50) to afford a white solid (3.42 g, 83%): $^1$H NMR (CD$_3$OD, 300 MHz) δ2.34 (s, 3H),), 8.09 (d, J=2.2 Hz, 1H), 8.42 (d, J=2.2 Hz, 1H).

19c. 7 a-(6-chloro-5-methyl-3-pyridinyl)-hexahydro-1H-pyrrolizine

2-Chloro-5-iodo-3-methylpyridine (1.0 g, 3.94 mmol) was dissolved in Et$_2$O and cooled to −95° C. A solution of 2.5M t-BuLi (1.7M in pentane, 5.1 mL, 7.67 mmol) in pentane was added dropwise. 1,2,3,5,6,7-hexahydropyrrolizinium perchlorate (1.2 g, 5.92 mmol) was added, and the reaction mixture was allowed to warm to −10° C. with stirring for 2 hours. The cold bath was removed, 2N HCl was added, and the phases were separated. The aqueous phase was basified with 15% NaOH and extracted with CH$_2$Cl$_2$ (2×). The CH$_2$Cl$_2$ fractions were combined, dried (MgSO$_4$) and concentrated, and the residue was chromatographed (silica gel; CHCl$_3$/MeOH, 99:1) to afford the title compound (694 mg, 74%): mg 31°–33° C.: $^1$H NMR (CDCl$_3$, 300 MHz) δ1.56–1.70 (m, 2H), 1.78–2.05 (m, 6H), 2.36 (s, 3H), 2.64–2.72 (m, 2H), 3.11–3.18 (m, 2H), 7.67 (d, J=2.0 Hz, 1H), 8.29 (d, J=2.0 Hz, 1H); MS (CI/NH$_3$) m/z: 237/239 (M+H)$^+$.

19d. 7a-(6-chloro-5-methyl-3-pyridinyl)-hexahydro-1H-pyrrolizine hydrochloride salt 7a-(6-Chloro-5-methyl-3-pyridinyl)-hexahydro-1H-pyrrolizine (245 mg, 1.03 mmol) was dissolved in Et$_2$O, and Et$_2$O saturated with HCl (g) was added. The solvent was removed, and the solid was crystallized from MeOH/Et$_2$O and dried to afford the title compound as white plates: mp 179°–180° C.; $^1$H NMR D$_2$O, 300 MHz) δ2.14–2.48 (m, 9H) 2.56–2.65 (m, 2H), 3.34–3.42 (m, 2H), 3.79–3.87 (m, 2H), 7.89 (d, J=3.0 Hz, 1H), 8.33 (d, J=3.0 Hz, 1H); MS (CI/NH$_3$) m/z: 237/239 (M+H)$^+$; MS (CI/NH$_3$): m/z 237 (M+H$^+$). Anal. Calcd for C$_{13}$H$_{17}$ClN$_2$.HCl.0.2 HCl: C, 55.67; H, 6.54; N, 9.99. Found: C, 55.90; H, 6.57; N, 9.76.

Example 20

7a-(6-methyl-3-pyridinyl)-hexahydro-1H-pyrrolizine hydrochloride salt 20a. 5-Amino-2-methylpyridine 2-Methyl-5-nitropyridine (1.4 g, 10 mmol) and 10% Pd/C (200 mg) were combined in MeOH (40mL) and allowed to stir under a H$_2$ atmosphere for 18 hours. The reaction mixture was filtered through celite and the filtrate concentrated. The residue was chromatographed (silica gel; CHCl$_3$/MeOH, 95:5) to afford the title compound (845 mg, 77%): $^1$H NMR (CD$_3$OD, 300 MHz) δ2.35 (s, 3H), 6.97–7.06 (m, 2H), 7.85 (d, J=2.5 Hz, 1H).

20b. 5-Iodo-2-methylpyridine

5-Amino-2-methylpyridine (825 mg, 7.6 mmol) in DME (4.0 mL) was added dropwise to a solution of boron trifluoride diethyl etherate (1.4 mL, 11.4 mmol) in DME (14.5 mL) at −17° C. After stirring for 15 min, t-butyl nitrite (1.1 mL, 9.2 mmol) in DME (14.5 mL) was carefully added to the reaction mixture while maintaining the temperature below −5° C. After complete addition the temperature was allowed to gradually warm to 5° C. over 1 hr. After recooling to −17° C., pentane was added and then decanted. The solid was triturated with pentane (2×) and Et$_2$O (2×) and then solvent was removed via positive N$_2$ pressure. The crude diazonium tetrafluoroborate salt was dissolved in acetonitrile (15 mL) and KI (1.4 g, 8.4 mmol) was added at −10° C. The reaction was allowed to gradually warm to ambient temperature and stir overnight. A solution of 10% sodium thiosulfate was carefully added to the reaction mixture which was then poured over Et$_2$O and the phases separated. The organic phase was dried (MgSO$_4$), concentrated and the residue chromatographed (silica gel; EtOAc/hexane, 1:15) to afford a pale white solid (315 mg, 83%): $^1$H NMR (CDCl$_3$, 300 MHz) δ2.50 (s, 3H),), 6.97 (d, J=8.1 Hz, 1H) 7.86 (dd, J=8.1, 2.0 Hz, 1H), 8.70 (d, J=2.0 Hz, 1H); MS (CI/NH$_3$) m/z: 220 (M+H)$^+$.

20c. 7a-(6-methyl-3-pyridinyl)-hexahydro-1H-pyrrolizine

5-Iodo-2-methylpyridine (345 mg, 1.39 mmol) was dissolved in Et$_2$O and cooled to −95° C. A solution of 2.5M t-BuLi (1.7M in pentane, 1.8 mL, 3.06 mmol) in pentane was added dropwise. 1,2,3,5,6,7-hexahydropyrrolizinium perchlorate (435 mg, 2.1 mmol) was added, and the reaction mixture was allowed to warm to −10° C. with stirring for 2 hours. The cold bath was removed, 2N HCl was added, and the phases were separated. The aqueous phase was basified with 15% NaOH and extracted with CH$_2$Cl$_2$ (2×). The CH$_2$Cl$_2$ fractions were combined, dried (MgSO$_4$) and concentrated, and the residue was chromatographed (silica gel; CHCl$_3$/MeOH, 95:5) to afford the title compound as an oil (126 mg, 45%): $^1$H NMR (CDCl$_3$, 300 MHz) δ1.57–1.71 (m, 2H), 1.77–2.05 (m, 6H), 2.52 (s, 3H), 2.64–2.72 (m, 2H), 3.12–3.19 (m, 2H), 7.05 (d, J=8.1 Hz, 1H), 7.71 (dd, J=8.1, 2.6 Hz, 1H), 8.56 (d, J=2.6 Hz, 1H); MS (CI/NH$_3$) m/z: 203 (M+H)$^+$.

20d. 7a-(6-methyl-3-pyridinyl)-hexahydro-1H-pyrrolizine dihydrochloride salt 7a-(6-methyl-3-pyridinyl)-hexahydro-1H-pyrrolizine (115 mg, 0.57 mmol) was dissolved in Et$_2$O, and Et$_2$O saturated with HCl (g) was added. The solvent was removed, and the solid was crystallized from MeOH/Et$_2$O and dried to afford the title compound as a free flowing white powder: mp 205°–208° C.; $^1$H NMR D$_2$O, 300 MHz) δ2.14–2.49 (m, 6H), 2.57–2.66 (m, 5H), 3.34–3.42 (m, 2H), 3.78–3.87 (m, 2H), 7.56 (d, J=8.1 Hz, 1H), 8.05 (dd, J=8.1, 2.7 Hz, 1H), 8.61 (d, J=2.7 Hz, 1H); MS (CI/NH$_3$) m/z: 203 (M+H)$^+$; MS (CI/NH$_3$): m/z 203 (M+H$^+$); Anal. Calcd for C$_{13}$H$_{18}$N$_2$.2 HCl.0.8 H$_2$O: C, 53.91; H, 7.52; N, 9.67. Found: C, 53.80; H, 7.46; N, 9.68.

Example 21

7a-(5-methyl-3-pyridinyl)-hexahydro-1H-pyrrolizine hydrochloride salt 21a. 7a-(5-methyl-3-pyridinyl)-hexahydro-1H-pyrrolizine 7a-(6-Chloro-5-methyl-3-pyridinyl)-hexahydro-1H-pyrrolizine (274 mg, 1.16 mmol, from Example 19c) and LAH (1.0M in THF, 1.2 mL, 1.16 mmol) were added to THF (4.5 mL), and the mixture was stirred at room temperature for 4 hours. An additional amount of LAH (1.0M in THF, 1.2 mL, 1.16 mmol) was added, and the reaction was stirred overnight. A further amount of LAH (2 equivalents) was added, and the reaction was stirred at room temperature for 24 hours and at 80° C. for 5 hours. The reaction was quenched with 10% $K_2CO_3$ solution, and the resulting slurry was filtered. The filtrate was diluted with EtOAc and 15% NaOH, and the phases were separated. The aqueous phase was extracted with methylene chloride, and all the organic solutions were combined, dried and concentrated. The residue was chromatographed (silica gel; $CHCl_3$/MeOH, 98:2) to afford the title compound as an oil (116 mg, 49%): $^1$H NMR ($CDCl_3$, 300 MHz) δ1.57–1.71 (m, 2H), 1.77–2.06 (m, 6H), 2.32 (s, 3H), 2.66–2.74 (m, 2H), 3.12–3.19 (m, 2H), 7.63 (s, 1H), 8.24 (s, 1H), 8.50 (s, 1H); MS (CI/$NH_3$) m/z: 203 (M+H)$^+$.

21b. 7a-(5-methyl-3-pyridinyl)-hexahydro-1H-pyrrolizine hydrochloride salt 7a-(5-methyl-3-pyridinyl)-hexahydro-1H-pyrrolizine (109 mg, 0.54 mmol) was dissolved in $Et_2O$, and $Et_2O$ saturated with HCl (g) was added. The solvent was removed, and the solid was triturated with $Et_2O$ and dried to afford the title compound as a white powder (112 mg, 87%); mp 153°–154° C.; $^1$H NMR $D_2O$, 300 MHz) δ2.12–2.49 (m, 9H), 2.57–2.66 (m, 2H), 3.34–3.43 (m, 2H), 3.79–3.87 (m, 2H), 7.90 (s, 1H), 8.46 (s, 1H), 8.52 (s, 1H); MS (CI/$NH_3$) m/z: 203 (M+H)$^+$; MS (CI/$NH_3$): m/z 203 (M+H+), 220 (M+$NH_4^+$). Anal. Calcd for $C_{13}H_{18}N_2$·1.4 HCl: C, 61.63; H, 7.72; N, 11.06. Found: C, 61.82; H, 7.89; N, 11.00.

Example 22

7a-(5-bromo-6-fluoro-3-pyridinyl)-hexahydro-1H-pyrrolizine hydrochloride salt 22a. 7a-(5-bromo-6-fluoro-3-pyridinyl)-hexahydro-1H-pyrrolizine n-BuLi (2.5M in hexanes, 0.252 mL, 0.63 mmol) was added to di-isopropylamine (0.082 mL, 0.63 mmol) in THF and stirred at room temperature for 10 minutes, then cooled to −78° C. 7a-(6-Fluoro-3-pyridinyl)-hexahydro-1H-pyrrolizine (123 mg, 0.60 mmol, from Example 12d) and 1,2-dibromo-1,1,2,2-tetrafluoroethane (0.215 mL, 1.80 mmol) were added. The mixture was slowly warmed to room temperature and stirred overnight. The reaction was quenched with 2N HCl, and the mixture was washed with $Et_2O$. The aqueous layer was basified with 15% NaOH and extracted with methylene chloride. The organic extracts were combined, dried, ($MgSO_4$) and concentrated. The residue was chromatographed (silica gel; $CHCl_3$/MeOH, 99:1) to afford the title compound as an oil (64 mg, 37%). $^1$H NMR ($CDCl_3$, 300 MHz) δ1.59–1.71 (m, 2H), 1.79–2.06 (m, 6H), 2.64–2.72 (m, 2H), 3.12–3.19 (m, 2H), 8.14 (dd, J=8.8, 2.2 Hz, 1H), 8.19 (dd, J=2.2, 1.2 Hz, 1H); MS (CI/$NH_3$) m/z: 285/287 (M+H)$^+$.

22b. 7a-(5-bromo-6-fluoro-3-pyridinyl)-hexahydro-1H-pyrrolizine hydrochloride salt 7a-(5-bromo-6-fluoro-3-pyridinyl)-hexahydro-1H-pyrrolizine was dissolved in $Et_2O$, and $Et_2O$ saturated with HCl (g) was added. The solvent was removed, and the solid was triturated with $Et_2O$ and dried to afford the title compound as a white powder (59 mg, 87%): mp 213°–215° C.; $^1$H NMR $D_2O$, 300 MHz) δ2.15–2.49 (m, 6H), 2.56–2.65 (m, 2H), 3.34–3.42 (m, 2H), 3.78–3.87 (m, 2H), 8.31 (dd, J=2.4, 1.0 Hz, 1H), 8.38 (dd, J=7.8, 2.4 Hz, 1H); MS (CI/$NH_3$) m/z: 285/287 (M+H)+; MS (CI/$NH_3$): m/z 285/287 (M+H$^+$). Anal. Calcd for $C_{12}H_{14}BrFN_2$·HCl: C, 44.81; H, 4.70; N, 8.71. Found: C, 45.04; H, 4.25; N, 8.48.

Example 23

7a-(5-chloro-6-fluoro-3-pyridinyl)-hexahydro-1H-pyrrolizine hydrochloride salt 7a-(5-chloro-6-fluoro-3-pyridinyl)-hexahydro-1H-pyrrolizine n-BuLi (2.5M in hexanes, 0.232 mL, 0.58 mmol) was added to di-isopropylamine (0.077 mL, 0.58 mmol) in THF and stirred at room temperature for 15 minutes, then cooled to −78° C. 7a-(6-Fluoro-3-pyridinyl)-hexahydro-1H-pyrrolizine (115 mg, 0.56 mmol, from Example 12d) and hexachloroethane (400 mg, 1.7 mmol) were added. The mixture was slowly warmed to room temperature and stirred overnight. The reaction was quenched with 2N HCl, and the mixture was washed with $Et_2O$. The aqueous layer was basified with 15% NaOH and extracted with methylene chloride. The organic extracts were combined, dried, ($MgSO_4$) and concentrated. The residue was chromatographed (silica gel; $CHCl_3$/MeOH, 99:1) to afford the title compound as an oil (45 mg, 34%): $^1$H NMR ($CDCl_3$, 300 MHz) δ1.60–1.72 (m, 2H), 1.80–2.06 (m, 6H), 2.64–2.72 (m, 2H), 3.14–3.27 (m, 2H), 8.00 (dd, J=8.8, 2.0 Hz, 1H), 8.15 (dd, J=2.0, 1.0 Hz, 1H); MS (CI/$NH_3$) m/z: 241 (M+H)$^+$.

7a-(5-chloro-6-fluoro-3-pyridinyl)-hexahydro-1H-pyrrolizine hydrochloride salt 7a-(5-chloro-6-fluoro-3-pyridinyl)-hexahydro-1H-pyrrolizine was dissolved in $Et_2O$, and $Et_2O$ saturated with HCl (g) was added. The solvent was removed, and the solid was triturated with $Et_2O$ and dried to afford the title compound as a white powder (35 mg, 74%): mp 181°–183° C.; $^1$H NMR ($D_2O$, 300 MHz) δ2.15–2.50 (m, 6H), 2.56–2.65 2H), 3.34–3.42 (m, 2H), 3.79–3.87 (m, 2H), 8.24–8.29 (m, 2H); MS (CI/$NH_3$) m/z: 241 (M+H)$^+$; MS (CI/$NH_3$): m/z 241/243 (M+H$^+$). Anal. Calcd for $C_{12}H_{14}ClFN_2$·HCl: C, 52.00; H, 5.45; N, 10.11. Found: C, 51.81; H, 5.62; N, 9.84.

Example 24

7a-(4-methyl-3-pyridinyl)-hexahydro-1H-pyrrolizine hydrochloride salt 24a. 3-Amino-4-methylpyridine 2-Chloro-4-methyl-3-nitropyridine (10.2 g, 59.1 mmol, Aldrich) and 10% Pd/C (1.5 g) were combined in MeOH (250 mL) under 4 atmospheres of $H_2$ for 20 hours at ambient temperature. The reaction mixture was filtered, and the filtrate was concentrated. The residue was chromatographed (silica gel; $CHCl_3$/MeOH, 95:5) to afford a white solid (6.1 g, 96%): $^1$H NMR ($CDCl_3$, 300 MHz) δ2.17 (s, 3H), 6.96 (d, J=4.8 Hz, 1H), 7.94 (d, J=4.8 Hz, 1H), 8.02 (s, 1H); MS (CI/$NH_3$) m/z: 109 (M+H)$^+$.

24b. 3-Iodo-4-methylpyridine

3-Amino-4-methylpyridine (2.0 g, 18.5 mmol) in DME (9.0 mL) was added dropwise to a solution of boron trifluoride diethyl etherate (3.4 mL, 27.7 mmol) in DME (35 mL) at −17° C. After stirring for 15 min, t-butyl nitrite (2.6 mL, 22.2 mmol) in DME (37.0 mL) was carefully added to the reaction mixture while maintaining the temperature below −5° C. After complete addition the temperature was allowed to gradually warm to 5° C. over 1 hr. After recooling to −17° C., pentane was added and decanted. The solid was triturated with pentane (2×) and Et$_2$O (2×), then the solvent was removed via positive N$_2$ pressure to afford a white solid. The crude diazonium tetrafluoroborate salt was dissolved in acetonitrile (70 mL) and KI (3.4 g, 20.3 mmol) was added at −10° C. The reaction was allowed to gradually warm to ambient temperature and stir overnight. A solution of 10% sodium thiosulfate was carefully added to the reaction mixture, which was then poured over Et$_2$O and the phases separated. The organic phase was dried (MgSO$_4$) and concentrated, and the residue was chromatographed (silica gel; EtOAc/hexane, 1:15) to afford an amber oil (2.2 mg, 54%): $^1$H NMR (CDCl$_3$, 300 MHz) δ2.42 (s, 3H), 7.19 (d, J=4.8 Hz, 1H), 8.38 (d, J=4.8 Hz, 1H), 8.86 (s, 1H).

24c. 7a-(4-methyl-3-pyridinyl)-hexahydro-1H-pyrrolizine

3-Iodo-4-methylpyridine (330 mg, 3.10 mmol) was dissolved in Et$_2$O and cooled to −95° C. A solution of t-BuLi (1.7M in pentane, 4.0 ml, 6.80 mmol) in pentane was added dropwise. 1,2,3,5,6,7-hexahydropyrrolizinium perchlorate (960 mg, 4.60 mmol) was added, and the reaction mixture was allowed to warm to −10° C. with stirring for 2 hours. The cold bath was removed, 2N HCl was added, and the phases were separated. The aqueous phase was basified with 15% NaOH and extracted with CH$_2$Cl$_2$ (2×). The CH$_2$Cl$_2$ fractions were combined, dried (MgSO$_4$) and concentrated, and the residue was chromatographed (silica gel; CHCl$_3$/MeOH, 99:1) to afford the title compound as an oil (41 mg, 6%): $^1$H NMR (CDCl$_3$, 300 MHz) δ1.54–1.69 (m, 2H), 1.77–1.89 (m, 2H), 1.93–2.11 (m, 4H), 2.41 (s, 3H), 2.69–2.77 (m, 2H), 3.08–3.15 (m, 2H), 7.02 (d, J=4.8 Hz, 1H), 8.32 (d, J=4.8 Hz, 1H), 9.06 (s, 1H); MS (CI/NH$_3$) m/z: 203 (M+H)$^+$.

24d. 7a-(4-methyl-3-pyridinyl)-hexahydro-1H-pyrrolizine dihydrochloride salt 7a-(4-methyl-3-pyridinyl)-hexahydro-1H-pyrrolizine (37 mg, 0.18 mmol) was dissolved in Et$_2$O, and Et$_2$O saturated with HCl (g) was added. The solvent was removed, and the solid was triturated with Et$_2$O and dried to afford the title compound as a white solid (26.2 mg, 61%): mp 244°–247° C.; $^1$H NMR (D$_2$O, 300 MHz) δ2.01–2.16 (m, 2H), 2.27–2.52 (m, 4H), 2.65 (s, 3H), 2.65–2.78 (m, 2H), 3.45–3.54 (m, 2H), 3.87–3.96 (m, 2H), 7.75 (d, J=5.6 Hz, 1H), 8.49 (s, 1H), 8.55 (d, J=5.6 Hz, 1H); MS (CI/NH$_3$): m/z 203 (M+H$^+$). Anal. Calcd for C$_{13}$H$_{18}$N$_2$·2 HCl: C, 56.73; H, 7.32; N, 10.18. Found: C, 56.94; H, 7.24; N, 9.99.

Example 25

7a-(5-phenyl-3-pyridinyl)-hexahydro-1H-pyrrolizine hydrochloride salt 25a. 3-bromo-5-phenylpyridine Portions of 3,5-dibromopyridine (1.0 g, 4.22 mmol), phenylboronic acid (570 mg, 4.6 mmol) and palladium tetra(triphenylphosphine) (60 mg) were combined in toluene (20 mL) with aqueous sodium carbonate solution (2M, 3.0 mL) and heated at reflux for 6 hours. The mixture was cooled to ambient temperature, and the solvent was removed. The residue was purified by chromatography (silica gel, eluting with ether:hexane 1:10 to give the title compound: MS (CI/NH$_3$) m/z: 234/236 (M+H)$^+$, 251/153 (M+NH$_4$)$^+$; $^1$H NMR (CDCl$_3$, 300 MHz) δ7.21–8.02 (dd, J=2.0, 2.0 Hz), 8.65 (d, J=2.0 Hz), 8.75 (d, J=2.0 Hz).

25b. 7a-(5-phenyl-3-pyridinyl)-hexahydro-1H-pyrrolizine

3-Bromo-3-phenylpyridine (200 mg, 0.85 mmol) was dissolved in Et$_2$O and cooled to −30° C. A solution of 2.5M t-BuLi (1.1 mL, 1.90 mmol) in pentane was added, and the reaction was stirred for 10 minutes. 1,2,3,5,6,7-Hexahydropyrrolizinium perchlorate (230 mg, 1.30 mmol) was added, and the reaction mixture was allowed to stir for 30 minutes at −30° C. then allowed to warm to room temperature and stir for 1 hour. Then 2N HCl was added, the phases were separated, and the aqueous phase was basified with 15% NaOH and extracted with CH$_2$Cl$_2$ (2×). The organic phases were combined, dried (MgSO$_4$) and concentrated, and the residue was chromatographed (silica gel; CHCl$_3$/MeOH, 95:5) to afford a clear oil (32.5 mg).

25c. 7a-(5-phenyl-3-pyridinyl)-hexahydro-1H-pyrrolizine hydrochloride salt

The 7a-(5-phenyl-3-pyridinyl)-hexahydro-1H-pyrrolizine compound from step 25b was dissolved in ether (5 mL) and Et$_2$O saturated with HCl (g) was added. The solvent was removed, and the solid was dried to afford the title compound as yellow needles (13.5 mg): mp 217°–220° C. (dec.); $^1$H NMR D$_2$O, 300 MHz) δ2.17–2.47 (m, 4H), 2.57–2.73 (m, 4H), 3.41–3.50 (m, 2H), 3.87–3.97 (m, 2H), 7.60–7.68 (m, 3H), 7.75–7.81 (m, 2H), 8.60 (dd, J=2.0, 2.0 Hz, 1H), 8.87 (d, J=2.0 Hz, 1H), 9.04 (d, J=2.0 Hz, 1H); MS (CI/NH$_3$) m/z: 265 (M+H)$^+$. Anal. Calcd for C$_{18}$H$_{20}$N$_2$·2.0 HCl·0.1 H$_2$O: C, 63.76; H, 6.60; N, 8.26. Found: C, 63.62; H, 6.48; N, 8.02.

What is claimed is:

1. A compound having the formula

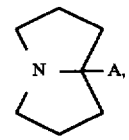

(I)

or a pharmaceutically acceptable salt or pro-drug thereof wherein the group designated A is selected from the group consisting of:

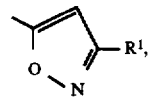

(a)

wherein R$^1$ is C$_1$–C$_3$-alkyl, —CH$_2$-aryl, —CH$_2$-substituted-aryl, or —CH$_2$–CH$_2$-substituted-aryl;

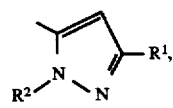

(b)

wherein R$^1$ is as defined above, and R$^2$ is H or C$_1$–C$_3$-alkyl;

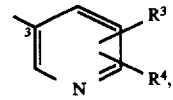

(c)

wherein

R$^3$ is substituted at the 2, 4, or 6-position and is selected from the group consisting of H, C$_1$–C$_3$-alkyl, Br, Cl, or F; and R$^4$ is substituted at one of the remaining positions not occupied by R$^3$ and is independently selected from the group consisting of H, C$_1$–C$_3$-alkyl, Br, Cl, F or C$_1$–C$_3$-alkyl-O—; or when substituted at the 5-position R$^4$ may additionally be selected from the group consisting of (1) —O—R$^6$, wherein R$^6$ is selected from the group consisting of;

(a) hydrogen, (b) alkyl of one to six carbon atoms,
(c) alkenyl of one to six carbon atoms
(d) alkynyl of one to six carbon atoms
(e) haloalkyl of one to six carbon atoms,
(f) hydroxyalkyl of two to six carbon atoms,
(h) amino,
(i) alkylamino of one to six carbon atoms,
(j) dialkylamino in which the two alkyl groups are independently of one to six carbon atoms,
(k) phenyl,
(l) naphthyl,
(m) biphenyl,
(n) furyl,
(o) thienyl,
(p) pyridinyl,
(q) pyrazinyl,
(r) pyridazinyl,
(s) pyrimidinyl,
(t) pyrrolyl,
(u) pyrazolyl,
(v) imidazolyl,
(w) indolyl,
(x) thiazolyl,
(y) oxazolyl,
(z) isoxazolyl,
(aa) thiadiazolyl,
(bb) oxadiazolyl,
(cc) quinolinyl,
(dd) isoquinolinyl,
(ee) aryl-$C_1$–$C_6$-alkyl,
(ff) heteroaryl-$C_1$–$C_6$-alkyl and
(gg) any of the groups (i) through (ff) of $R^6$ above substituted with one or two substituents independently selected from the group consisting of alkyl of one to six carbon atoms, haloalkyl of one to six carbon atoms, alkoxy of one to six carbon atoms, alkoxyalkyl in which the alkoxy and alkyl portions are independently of one to six carbon atoms, alkoxyalkoxy in which the alkoxy portions are independently of one to six carbon atoms, halogen, cyano, hydroxy, amino, alkylamino of one to six atoms, carboxyl, and alkoxycarbonyl of two to six carbon atoms;

(2) —S—$R^6$, wherein $R^6$ is as defined above;
(3) —N($R^6$)($R^7$), wherein $R^6$ is as defined above and $R^7$ is selected from H or alkyl of 1 to 6 carbon atoms;
(4) L$R^8$, wherein L is absent or is selected from the group consisting
(a) —(CH$_2$)$_p$—, wherein p is 1 to 6;
(b) —(CH=CH)$_q$—, wherein q is one or two;
(c) —C(O)—;
(d) —OC(O)—;
(e) —N($R^7$)—C(O)—, wherein $R^7$ is as defined above;
(f) —CH$_2$—CH$_2$—C(O)—;
(g) —CH$_2$—O—C(O)—; —CH$_2$—NH—C(O)—; or
(h) —C≡C—; and
wherein-$R^8$ is selected from the group consisting of:
(a) hydrogen,
(b) alkyl of one to six carbon atoms,
(c) alkenyl of one to six carbon atoms
(d) alkynyl of one to six carbon atoms
(e) haloalkyl of one to six carbon atoms,
(f) hydroxyalkyl of one to six carbon atoms,
(g) alkoxy of one to six carbon atoms,
(h) amino,
(i) alkylamino of one to six carbon atoms,
(j) dialkylamino in which the two alkyl groups are independently of one to six carbon atoms,
(k) phenyl,
(l) naphthyl,
(m) biphenyl,
(n) furyl,
(o) thienyl,
(p) pyridinyl,
(q) pyrazinyl,
(r) pyridazinyl,
(s) pyrimidinyl,
(t) pyrrolyl,
(u) pyrazolyl,
(v) imidazolyl,
(w) indolyl,
(x) thiazolyl,
(y) oxazolyl,
(z) isoxazolyl,
(aa) thiadiazolyl,
(bb) oxadiazolyl,
(cc) quinolinyl,
(dd) isoquinolinyl, and
(ee) any of the groups (i) through (dd) of $R^6$ above substituted with one or two substituents independently selected from the group consisting of alkyl of one to six carbon atoms, haloalkyl of one to six carbon atoms, alkoxy of one to six carbon atoms, alkoxyalkyl in which the alkoxy and alkyl portions are independently of one to six carbon atoms, alkoxyalkoxyl in which the alkoxy portions are independently of one to six carbon atoms, halogen, cyano, hydroxy, amino, alkylamino of one to six carbon atoms, carboxyl, and alkoxycarbonyl of two to six carbon atoms;

with the requirement that in groups of the type —O—$R^6$, —S—$R^6$, —N($R^6$)($R^7$) and L—$R^8$, none of $R^6$, —N($R^6$)($R^7$) or —L—$R^8$ may contain a nitrogen atom which is in conjugation with a double or triple bond;

(d) 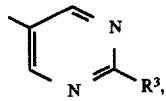

wherein $R^3$ is as defined above;

(e) 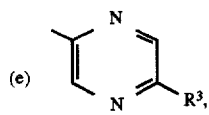

wherein $R^3$ is as defined above;

(f) 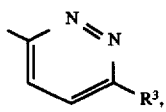

wherein $R^3$ is as defined above; and (g) 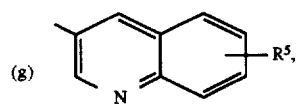

wherein $R^5$ is H, $C_1$–$C_3$-alkyl, Cl or F.

2. A compound according to claim 1, wherein A is selected from options (a) and (c).

3. A compound according to claim 2, wherein A is selected from option (c).

4. A compound according to claim 1 which is 7a-(3-methyl-5-isoxazolyl)-hexahydro-1H-pyrrolizine;
7a-(1H-3-methyl-5-pyrazolyl)-hexahydro-1H-pyrrolizine;
7a-(3-pyridinyl)-hexahydro-1H-pyrrolizine;
7a-(3-quinolinyl)-hexahydro-1H-pyrrolizine;
7a-(6-chloro-3-pyridinyl)-hexahydro-1H-pyrrolizine;
7a-(2-fluoro-3-pyridinyl)-hexahydro-1H-pyrrolizine;
7a-(2-chloro-3-pyridinyl)-hexahydro-1H-pyrrolizine;
7a-(5,6-dichloro-3-pyridinyl)-hexahydro-1H-pyrrolizine;
7a-(5-pyrimidinyl)-hexahydro-1H-pyrrolizine;
7a-(2,6-difluoro-3-pyridinyl)-hexahydro-1H-pyrrolizine;
7a-(2,6-dichloro-3-pyridinyl)-hexahydro-1H-pyrrolizine;
7a-(6-fluoro-3-pyridinyl)-hexahydro-1H-pyrrolizine;
7a-(3-ethyl-5-isoxazolyl)-hexahydro-1H-pyrrolizine;
7a-(3-propyl-5-isoxazolyl)-hexahydro-1H-pyrrolizine;
7a-(3-benzyl-5-isoxazolyl)-hexahydro-1H-pyrrolizine;
7a-(5-hydroxy-3-pyridinyl)-hexahydro-1H-pyrrolizine;
7a-(5-benzyloxy-3-pyridinyl)-hexahydro-1H-pyrrolizine;
7a-(5-bromo-3-pyridinyl)-hexahydro-1H-pyrrolizine;
7a-(6-fluoro-5-methyl-3-pyridinyl)-hexahydro-1H-pyrrolizine;
7a-(6-chloro-5-methyl-3-pyridinyl)-hexahydro-1H-pyrrolizine;
7a-(6-methyl-3-pyridinyl)-hexahydro-1H-pyrrolizine;
7a-(5-methyl-3-pyridinyl)-hexahydro-1H-pyrrolizine;
7a-(5-bromo-6-fluoro-3-pyridinyl)-hexahydro-1H-pyrrolizine;
7a-(5-chloro-6-fluoro-3-pyridinyl)-hexahydro-1H-pyrrolizine;
7a-(4-methyl-3-pyridinyl)-hexahydro-1H-pyrrolizine; or
7a-(5-phenyl-3-pyridinyl)-hexahydro-1H-pyrrolizine.

5. A compound according to claim 1 wherein the compound has binding affinity at both an alpha-4-beta-2 nicotinic receptor subtype and an alpha-7 nicotinic receptor subtype.

6. A pharmaceutical composition comprising a therapeutically-effective amount of a compound of formula (I) in combination with a pharmaceutically acceptable carrier.

7. A method for selectively controlling nicotine acetylcholine synaptic transmission in a mammal comprising administering a therapeutically-effective amount of a compound of formula (I) to a patient in need of treatment thereof.

* * * * *